US012729371B2

(12) United States Patent
Latroche et al.

(10) Patent No.: US 12,729,371 B2
(45) Date of Patent: Sep. 8, 2026

(54) COMPOSITIONS AND METHODS FOR HAEMATOPOIETIC STEM CELL TRANSPLANTATION

(71) Applicants: Ospedale San Raffaele S.r.l., Milan (IT); Fondazione Telethon, Rome (IT)

(72) Inventors: Claire Latroche, Milan (IT); Luigi Naldini, Milan (IT); Maura Manzi, Milan (IT)

(73) Assignees: Ospedale San Raffaele S.r.l., Milan (IT); Fondazione Telethon, Rome (IT)

( * ) Notice: Subject to any disclaimer, the term of this patent is extended or adjusted under 35 U.S.C. 154(b) by 1071 days.

(21) Appl. No.: 17/250,050

(22) PCT Filed: May 16, 2019

(86) PCT No.: PCT/EP2019/062666
§ 371 (c)(1),
(2) Date: Nov. 13, 2020

(87) PCT Pub. No.: WO2019/219838
PCT Pub. Date: Nov. 21, 2019

(65) Prior Publication Data

US 2021/0317411 A1 Oct. 14, 2021

(30) Foreign Application Priority Data

May 16, 2018 (GB) ..................................... 1807944

(51) Int. Cl.

| | |
|---|---|
| ***C12N 5/0789*** | (2010.01) |
| ***A61K 35/28*** | (2015.01) |
| *A61K 35/12* | (2015.01) |
| *A61K 48/00* | (2006.01) |
| *C07K 14/705* | (2006.01) |
| *C07K 14/715* | (2006.01) |

(52) U.S. Cl.
CPC ............ *C12N 5/0647* (2013.01); *A61K 35/28* (2013.01); *A61K 2035/124* (2013.01); *C12N 2501/58* (2013.01); *C12N 2501/599* (2013.01); *C12N 2510/00* (2013.01)

(58) Field of Classification Search
CPC ... C12N 5/0647; C12N 2510/00; A61K 35/28
See application file for complete search history.

(56) References Cited

U.S. PATENT DOCUMENTS

2011/0268712 A1* 11/2011 Lapidot ................ C12N 5/0647 435/372
2016/0324982 A1 11/2016 Scadden et al.

FOREIGN PATENT DOCUMENTS

WO WO-98/05635 A1 2/1998
WO WO-98/07859 A2 2/1998
WO WO-98/09985 A2 3/1998
WO WO-2003082305 A1 10/2003
WO WO-2017078100 A1 5/2017
WO WO-2017/218948 A2 12/2017
WO WO-2018/033254 A2 2/2018

OTHER PUBLICATIONS

Gul-Uldag et al., (2011) Cationic liposome-mediated CXCR4 gene delivery into hematopoietic stem/progenitor cells: Implications for clinical transplantation and gene therapy. Stem Cells and Development, 21(10): 1587-1596. (Year: 2011).*
Khan et al., (2004) Overexpression of CXCR4 on human CD34+ progenitors increases their proliferation, migration, and NOD/SCID repopulation. Gene Therapy, 103(8): 2942-2949 (Year: 2004).*
Brenner et al., (2004) CXCR4-transgene expression significantly improves marrow engraftment of cultured hematopoietic stem cells. Stem Cells, 22: 1128-1133 (Year: 2004).*
Ryser et al., (2008) mRNA transfection of CXCR4-GFP fusion-simply generated by PCR-results in efficient migration of primary human mesenchymal stem cells. Tissue Engineering Part D: Methods, 14(3), pp. 177-184 (Year: 2008).*
Nagree et al., (2015) Towards in vivo amplification: overcoming hurdles in the use of hematopoietic stem cells in transplantation and gene therapy. World Journal of Stem Cells, 7(11) pp. 1233-1250 (Year: 2015).*
"Two bright new faces in gene therapy", Nat. Biotechnol., 14(5):556 (1996).
Ausubel et al. Short Protocols in Molecular Biology, 4th edition, (1999), pp. 7-58 to 7-60.
Banaszynski et al., Hira-Dependent Histone H3.3 Deposition Facilitates PRC2 Recruitment at Developmental Loci in ES Cells, Cell, 2012, vol. 155, No. 1, pp. 107-120.
Cartier et al., [Gene therapy of x-linked adrenoleukodystrophy using hematopoietic stem cells and a lentiviral vector], Bull. Acad. Natl. Med., 194(2):255-64 (2010). [Article in French, English abstract provided].
Domingues et al., New agents in HSC mobilization, International Journal of Hematology, 2017, vol. 105, pp. 141-152.
Welschinger et al., Plerixafor (AMD3100) induces prolonged mobilization of acute lymphoblastic leukemia cells and increases the proportion of cycling cells in the blood in mice, Exp Hematol, (2013), vol. 41, pp. 293-302.
Aiuti et al., Gene therapy for immunodeficiency due to adenosine deaminase deficiency, N. Engl. J. Med., 360(5):447-58 (Jan. 2009).
Aiuti et al., Lentiviral hematopoietic stem cell gene therapy in patients with Wiskott-Aldrich syndrome, Science, 341(6148):1233151 (Aug. 2013).
Altschul et al., Basic Local Alignment Search Tool, J. Mol. Biol., 215:403-10 (1990).
Ausubel et al., Current Protocols in Molecular Biology, John Wiley and Sons, chapters 9, 13, 16 (1995).

(Continued)

*Primary Examiner* — Kara D Johnson
(74) *Attorney, Agent, or Firm* — MARSHALL, GERSTEIN & BORUN LLP

(57) ABSTRACT

Use of CD47 and/or C-X-C chemokine receptor type 4 (CXCR4) for increasing engraftment by haematopoietic stem and/or progenitor cells (HSPCs).

8 Claims, 12 Drawing Sheets

Specification includes a Sequence Listing.

(56) References Cited

OTHER PUBLICATIONS

Ausubel et al., Short Protocols in Molecular Biology, 4th edition, Ch. 18 (1999).
Biffi et al., Lentiviral hematopoietic stem cell gene therapy benefits metachromatic leukodystrophy, Science, 341(6148):1233158 (Aug. 2013).
Boztug et al., Stem-cell gene therapy for the Wiskott-Aldrich syndrome, N. Engl. J. Med., 363(20): 1918-27 (Nov. 2010).
Cartier et al., Hematopoietic stem cell gene therapy with a lentiviral vector in X-linked adrenoleukodystrophy, Science, 326(5954):818-23 (Nov. 2009).
Chang et al., The genetic engineering of hematopoietic stem cells: the rise of lentiviral vectors, the conundrum of the ltr, and the promise of lineage-restricted vectors, Mol. Ther., 15(3):445-56 (2007).
Czechowicz et al., Immune sparing conditioning for BMT/HSCT using anti-Ckit immunotoxins, Biol. Bone Marrow Transplant, 24:S60 Abstract 54 (2018).
Dahlman et al., Orthogonal gene knockout and activation with a catalytically active Cas9 nuclease, Nat. Biotechnol., 33(11):1159-61 (2015).
Devereux et al., A comprehensive set of sequence analysis programs for the VAX, Nucleic Acids Res., 12(1 Pt. 1):387-95 (1984).
Esvelt et al., Orthogonal Cas9 proteins for RNA-guided gene regulation and editing, Nat. Methods, 10(11):1116-21 (2013).
Fukuda et al., The chemokine GRObeta mobilizes early hematopoietic stem cells characterized by enhanced homing and engraftment, Blood, 110(3):860-9 (2007).
Gaj et al., ZFN, TALEN and CRISPR/Cas-based methods for genome engineering, Trends Biotechnol., vol. 31, pp. 397-405 (2013).
Hacien-Bey-Abina et al., Efficacy of gene therapy for X-linked severe combined immunodeficiency, N. Engl. J. Med., 363(4):355-64 (Jul. 2010).
International Application No. PCT/EP2019/062666, International Search Report and Written Opinion, mailed Sep. 6, 2019.
Kahn et al., Overexpression of CXCR4 on human CD34+ progenitors increases their proliferation, migration, and NOD/SCID repopulation, Blood, 103(8):2942-9 (2004).
Latroche et al., Development of a new generation of gene-edited HSC to induce engraftment advantage and favour outgrowth in vivo, Mol. Therapy, ASGCT 21st Annual Meeting Abstracts, 26(5)(S1), p. 18, May 8, 2018.
Legrand et al., Functional CD47/signal regulatory protein alpha (SIRP(alpha)) interaction is required for optimal human T- and natural killer—(NK) cell homeostasis in vivo, Proc. Natl. Acad. Sci. USA, 108(32):13224-9 (2011).
Lilley et al. (eds.), DNA Structures, Part A, Synthesis and Physical Analysis of DNA, vol. 211 in Methods in Enzymology, San Diego, California: Academic Press, Inc. (1992).
Paix et al., High Efficiency, Homology-Directed Genome Editing in Caenorhabditis elegans Using CRISPR-Cas9 Ribonucleoprotein Complexes, Genetics, 201(1):47-54 (2015).
Palchaudhuri et al., Non-genotoxic conditioning for hematopoietic stem cell transplantation using a hematopoietic-cell-specific internalizing immunotoxin, Nat. Biotechnol., 34(7):738-45 (2016).
Polak et al. (eds.), In Situ Hybridization: Principles and Practice, New York: Oxford University Press (1990).
Ramirez et al., BIO5192, a small molecule inhibitor of VLA-4, mobilizes hematopoietic stem and progenitor cells, Blood, 114(7):1340-3 (2009).
Reid et al., CXCL12/CXCR4 Signaling Enhances Human PSC-Derived Hematopoietic Progenitor Function and Overcomes Early In Vivo Transplantation Failure, Stem Cell Reports, 10(5):1625-41 (2018).
Roe et al., DNA Isolation and Sequencing: Essential Techniques, Chichester, West Sussex: John Wiley & Sons (1996).
Sambrook et al., Molecular Cloning: a Laboratory Manual, Cold Harbor Laboratory, 2nd edition (1989).
Sander et al., CRISPR-Cas systems for editing, regulating and targeting genomes, Nat. Biotechnol., 32(4):347-55 (2014).
Silva et al., Meganucleases and other tools for targeted genome engineering: perspectives and challenges for gene therapy, Curr. Gene Ther., 11(1):11-27 (2011).
Tatusova et al., BLAST 2 Sequences, a new tool for comparing protein and nucleotide sequences, FEMS Microbiol. Lett., 174(2):247-50 (1999).
Tatusova et al., Erratum to "Blast 2 Sequences, a new tool for comparing protein and nucleotide sequences", FEMS Microbiol. Lett., 177:187-8 (1999).
Van der Oost et al., Unravelling the structural and mechanistic basis of CRISPR-Cas systems, Nat. Rev. Microbiol., 12(7):479-92 (2014).
Wang et al., Attenuation of phagocytosis of xenogeneic cells by manipulating CD47, Blood, 109(2):836-42 (2007).
Zalatan et al., Engineering complex synthetic transcriptional programs with CRISPR RNA scaffolds, Cell, 160(1):339-50 (2015).
Zetsche et al., Cpf1 is a single RNA-guided endonuclease of a class 2 CRISPR-Cas system, Cell, 163(3):759-71 (2015).

* cited by examiner

SEQUENCE LISTING

```
<160> NUMBER OF SEQ ID NOS: 18

<210> SEQ ID NO 1
<211> LENGTH: 972
<212> TYPE: DNA
<213> ORGANISM: Artificial Sequence
<220> FEATURE:
<223> OTHER INFORMATION: nucleotide sequence encoding cluster of
      differentiation 47 (CD47)

<400> SEQUENCE: 1

atgtggcccc tggtagcggc gctgttgctg ggctcggcgt gctgcggatc agctcagcta     60

ctatttaata aaacaaaatc tgtagaattc acgttttgta atgacactgt cgtcattcca    120

tgctttgtta ctaatatgga ggcacaaaac actactgaag tatacgtaaa gtggaaattt    180

aaaggaagag atatttacac ctttgatgga gctctaaaca agtccactgt ccccactgac    240

tttagtagtg caaaaattga agtctcacaa ttactaaaag gagatgcctc tttgaagatg    300

gataagagtg atgctgtctc acacacagga aactacactt gtgaagtaac agaattaacc    360

agagaaggtg aaacgatcat cgagctaaaa tatcgtgttg tttcatggtt ttctccaaat    420

gaaaatattc ttattgttat tttcccaatt tttgctatac tcctgttctg gggacagttt    480

ggtattaaaa cacttaaata tagatccggt ggtatggatg agaaaacaat tgctttactt    540

gttgctggac tagtgatcac tgtcattgtc attgttggag ccattctttt cgtcccaggt    600

gaatattcat taaagaatgc tactggcctt ggtttaattg tgacttctac agggatatta    660

atattacttc actactatgt gtttagtaca gcgattggat taacctcctt cgtcattgcc    720

atattggtta ttcaggtgat agcctatatc ctcgctgtgg ttggactgag tctctgtatt    780

gcggcgtgta taccaatgca tggccctctt ctgatttcag gtttgagtat cttagctcta    840

gcacaattac ttggactagt ttatatgaaa tttgtggctt ccaatcagaa gactatacaa    900

cctcctagga aagctgtaga ggaacccctt aatgcattca aagaatcaaa aggaatgatg    960

aatgatgaat aa                                                         972


<210> SEQ ID NO 2
<211> LENGTH: 323
<212> TYPE: PRT
<213> ORGANISM: Artificial Sequence
<220> FEATURE:
<223> OTHER INFORMATION: CD47 sequence

<400> SEQUENCE: 2

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80
```

```
Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu


<210> SEQ ID NO 3
<211> LENGTH: 292
<212> TYPE: PRT
<213> ORGANISM: Artificial Sequence
<220> FEATURE:
<223> OTHER INFORMATION: CD47 sequence

<400> SEQUENCE: 3

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110
```

```
Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val
    290


<210> SEQ ID NO 4
<211> LENGTH: 305
<212> TYPE: PRT
<213> ORGANISM: Artificial Sequence
<220> FEATURE:
<223> OTHER INFORMATION: CD47 sequence

<400> SEQUENCE: 4

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175
```

```
Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
    290                 295                 300

Asn
305


<210> SEQ ID NO 5
<211> LENGTH: 311
<212> TYPE: PRT
<213> ORGANISM: Artificial Sequence
<220> FEATURE:
<223> OTHER INFORMATION: CD47 sequence

<400> SEQUENCE: 5

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220
```

```
Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn
305                 310


<210> SEQ ID NO 6
<211> LENGTH: 1059
<212> TYPE: DNA
<213> ORGANISM: Artificial Sequence
<220> FEATURE:
<223> OTHER INFORMATION: nucleotide sequence encoding C-X-C chemokine
      receptor type 4 (CXCR4)

<400> SEQUENCE: 6

atggagggga tcagtatata cacttcagat aactacaccg aggaaatggg ctcaggggac      60

tatgactcca tgaaggaacc ctgtttccgt gaagaaaatg ctaatttcaa taaaatcttc     120

ctgcccacca tctactccat catcttctta actggcattg tgggcaatgg attggtcatc     180

ctggtcatgg gttaccagaa gaaactgaga agcatgacgg acaagtacag gctgcacctg     240

tcagtggccg acctcctctt tgtcatcacg cttcccttct gggcagttga tgccgtggca     300

aactggtact ttgggaactt cctatgcaag gcagtccatg tcatctacac agtcaacctc     360

tacagcagtg tcctcatcct ggccttcatc agtctggacc gctacctggc catcgtccac     420

gccaccaaca gtcagaggcc aaggaagctg ttggctgaaa aggtggtcta tgttggcgtc     480

tggatccctg ccctcctgct gactattccc gacttcatct ttgccaacgt cagtgaggca     540

gatgacagat atatctgtga ccgcttctac cccaatgact tgtgggtggt tgtgttccag     600

tttcagcaca tcatggttgg ccttatcctg cctggtattg tcatcctgtc ctgctattgc     660

attatcatct ccaagctgtc acactccaag ggccaccaga agcgcaaggc cctcaagacc     720

acagtcatcc tcatcctggc tttcttcgcc tgttggctgc cttactacat tgggatcagc     780

atcgactcct tcatcctcct ggaaatcatc aagcaagggt gtgagtttga gaacactgtg     840

cacaagtgga tttccatcac cgaggcccta gctttcttcc actgttgtct gaaccccatc     900

ctctatgctt tccttggagc caaatttaaa acctctgccc agcacgcact cacctctgtg     960

agcagagggt ccagcctcaa gatcctctcc aaaggaaagc gaggtggaca ttcatctgtt    1020

tccactgagt ctgagtcttc aagttttcac tccagctaa                          1059


<210> SEQ ID NO 7
<211> LENGTH: 352
<212> TYPE: PRT
<213> ORGANISM: Artificial Sequence
<220> FEATURE:
<223> OTHER INFORMATION: CXCR4 sequence

<400> SEQUENCE: 7

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
```

```
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350


<210> SEQ ID NO 8
<211> LENGTH: 969
<212> TYPE: DNA
<213> ORGANISM: Artificial Sequence
<220> FEATURE:
<223> OTHER INFORMATION: nucleotide sequence encoding CD47

<400> SEQUENCE: 8

atgtggcctc tcgtggccgc tctgctgctc gggagcgctt gttgcggcag cgcccagctg     60

ctgttcaaca aaaccaagtc cgtcgagttc accttctgca acgacacagt ggtgatcccc    120

tgcttcgtca ccaacatgga ggctcagaat accaccgagg tctacgtcaa gtggaaattc    180

aagggcagag acatctacac cttcgacgga gccctcaaca agagcacagt gcctaccgac    240
```

```
ttttccagcg ccaagattga ggtgagccaa ctcctgaagg gagacgccag cctgaagatg    300

gacaagagcg atgccgtcag ccacacagga aactacacct gcgaggtgac agagctcacc    360

agagagggcg agaccatcat cgagctcaaa tacagagtgg tgtcctggtt ctcccccaac    420

gagaacatcc tcatcgtgat cttccccatc ttcgccatcc tgctgttctg ggccagttc     480

ggcatcaaaa ccctgaagta tagatccggc ggcatggacg agaaaacaat cgccctgctg    540

gtggccggcc tcgtgattac cgtgatcgtc atcgtgggcg ccatcctctt cgtgcccgga    600

gagtacagcc tcaagaacgc caccggcctg ggcctgattg tgacctccac aggcattctg    660

atcctgctgc actactacgt gttcagcaca gccattggcc tcacaagctt cgtgatcgcc    720

atcctggtca tccaggtgat cgcctacatc ctcgccgtgg tcggactcag cctctgtatt    780

gccgcttgca tccccatgca cggacccctc ctgatctccg gcctcagcat tctggctctc    840

gctcagctgc tcggcctggt gtacatgaag ttcgtcgcca gcaaccagaa gaccatccaa    900

ccccccagaa aggccgtcga agagcctctg aacgccttta aggagagcaa gggcatgatg    960

aacgacgag                                                            969
```

<210> SEQ ID NO 9
<211> LENGTH: 1071
<212> TYPE: DNA
<213> ORGANISM: Artificial Sequence
<220> FEATURE:
<223> OTHER INFORMATION: nucleotide sequence encoding CXCR4

<400> SEQUENCE: 9

```
atgtctattc ctctgcccct gctgcagatc tacaccagcg acaactacac cgaggaaatg     60

ggcagcggcg actacgacag catgaaggaa ccctgcttcc gggaagagaa cgccaacttc    120

aacaagatct tcctgcccac aatctacagc atcatctttc tgaccggcat cgtgggcaac    180

ggactcgtga tcctcgtgat gggctaccag aaaaagctgc ggagcatgac cgacaagtac    240

cggctgcacc tgagcgtggc cgacctgctg ttcgtgatca ccctgccttt ctgggccgtg    300

gacgccgtgg ccaattggta cttcggcaac ttcctgtgca aggccgtgca cgtgatctac    360

acagtgaacc tgtacagcag cgtgctgatc ctggccttca tcagcctgga cagatacctg    420

gccatcgtgc acgccaccaa cagccagcgg cctagaaagc tgctggccga gaaggtggtg    480

tacgtgggcg tgtggattcc cgccctgctg ctgaccatcc ccgacttcat cttcgccaac    540

gtgtccgagg ccgacgaccg gtacatctgc gaccggttct accccaacga cctgtgggtg    600

gtggtgttcc agttccagca catcatggtg ggactgatcc tgcctggcat cgtgattctg    660

agctgctact gcatcatcat cagcaagctg agccacagca agggccacca gaagcggaag    720

gccctgaaaa ccaccgtgat cctgattctg gctttcttcg cctgctggct gccctactac    780

atcggcatca gcatcgacag cttcatcctg ctggaaatca tcaagcaggg ctgcgagttc    840

gagaacaccg tgcacaagtg gatcagcatt accgaggccc tggccttttt ccactgctgc    900

ctgaacccta tcctgtacgc cttcctgggc gccaagttca agacctctgc ccagcacgcc    960

ctgaccagcg tgtccagagg aagcagcctg aagatcctga gcaagggcaa gagaggcggc   1020

cacagctccg tgtctacaga gagcgagagc agcagcttcc acagcagctg a            1071
```

<210> SEQ ID NO 10
<211> LENGTH: 1071
<212> TYPE: DNA
<213> ORGANISM: Artificial Sequence
<220> FEATURE:

<223> OTHER INFORMATION: nucleotide sequence encoding CXCR4

<400> SEQUENCE: 10

```
atgtccattc ctttgcctct tttgcagata tacacttcag ataactacac cgaggaaatg     60
ggctcagggg actatgactc catgaaggaa ccctgtttcc gtgaagaaaa tgctaatttc    120
aataaaatct tcctgcccac catctactcc atcatcttct taactggcat tgtgggcaat    180
ggattggtca tcctggtcat gggttaccag aagaaactga gaagcatgac ggacaagtac    240
aggctgcacc tgtcagtggc cgacctcctc tttgtcatca cgcttccctt ctgggcagtt    300
gatgccgtgg caaactggta ctttgggaac ttcctatgca aggcagtcca tgtcatctac    360
acagtcaacc tctacagcag tgtcctcatc ctggccttca tcagtctgga ccgctacctg    420
gccatcgtcc acgccaccaa cagtcagagg ccaaggaagc tgttggctga aaaggtggtc    480
tatgttggcg tctggatccc tgccctcctg ctgactattc ccgacttcat ctttgccaac    540
gtcagtgagg cagatgacag atatatctgt gaccgcttct accccaatga cttgtgggtg    600
gttgtgttcc agtttcagca catcatggtt ggccttatcc tgcctggtat tgtcatcctg    660
tcctgctatt gcattatcat ctccaagctg tcacactcca agggccacca gaagcgcaag    720
gccctcaaga ccacagtcat cctcatcctg gctttcttcg cctgttggct gccttactac    780
attgggatca gcatcgactc cttcatcctc ctggaaatca tcaagcaagg gtgtgagttt    840
gagaacactg tgcacaagtg gatttccatc accgaggccc tagctttctt ccactgttgt    900
ctgaacccca tcctctatgc tttccttgga gccaaattta aaacctctgc ccagcacgca    960
ctcacctctg tgagcagagg gtccagcctc aagatcctct ccaaaggaaa gcgaggtgga   1020
cattcatctg tttccactga gtctgagtct tcaagttttc actccagcta a            1071
```

<210> SEQ ID NO 11
<211> LENGTH: 1059
<212> TYPE: DNA
<213> ORGANISM: Artificial Sequence
<220> FEATURE:
<223> OTHER INFORMATION: nucleotide sequence encoding CXCR4

<400> SEQUENCE: 11

```
atggaaggca tcagcatcta caccagcgac aactacaccg aggaaatggg cagcggcgac     60
tacgacagca tgaaggaacc ctgcttccgg gaagagaacg ccaacttcaa caagatcttc    120
ctgcccacaa tctacagcat catctttctg accggcatcg tgggcaacgg actcgtgatc    180
ctcgtgatgg gctaccagaa aaagctgcgg agcatgaccg acaagtaccg gctgcacctg    240
agcgtggccg acctgctgtt cgtgatcacc ctgcctttct gggccgtgga cgccgtggcc    300
aattggtact tcggcaactt cctgtgcaag gccgtgcacg tgatctacac agtgaacctg    360
tacagcagcg tgctgatcct ggccttcatc agcctggaca gatacctggc catcgtgcac    420
gccaccaaca gccagcggcc tagaaagctg ctggccgaga aggtggtgta cgtgggcgtg    480
tggattcccg ccctgctgct gaccatcccc gacttcatct tcgccaacgt gtccgaggcc    540
gacgaccggt acatctgcga ccggttctac cccaacgacc tgtgggtggt ggtgttccag    600
ttccagcaca tcatggtggg actgatcctg cctggcatcg tgattctgag ctgctactgc    660
atcatcatca gcaagctgag ccacagcaag ggccaccaga agcggaaggc cctgaaaacc    720
accgtgatcc tgattctggc tttcttcgcc tgctggctgc cctactacat cggcatcagc    780
atcgacagct tcatcctgct ggaaatcatc aagcagggct gcgagttcga gaacaccgtg    840
cacaagtgga tcagcattac cgaggccctg gcctttttcc actgctgcct gaaccctatc    900
```

```
ctgtacgcct tcctgggcgc caagttcaag acctctgccc agcacgccct gaccagcgtg    960

tccagaggaa gcagcctgaa gatcctgagc aagggcaaga gaggcggcca cagctccgtg   1020

tctacagaga gcgagagcag cagcttccac agcagctga                          1059


<210> SEQ ID NO 12
<211> LENGTH: 356
<212> TYPE: PRT
<213> ORGANISM: Artificial Sequence
<220> FEATURE:
<223> OTHER INFORMATION: CXCR4 sequence

<400> SEQUENCE: 12

Met Ser Ile Pro Leu Pro Leu Leu Gln Ile Tyr Thr Ser Asp Asn Tyr
1               5                   10                  15

Thr Glu Glu Met Gly Ser Gly Asp Tyr Asp Ser Met Lys Glu Pro Cys
            20                  25                  30

Phe Arg Glu Glu Asn Ala Asn Phe Asn Lys Ile Phe Leu Pro Thr Ile
        35                  40                  45

Tyr Ser Ile Ile Phe Leu Thr Gly Ile Val Gly Asn Gly Leu Val Ile
    50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Ile Thr Leu Pro
                85                  90                  95

Phe Trp Ala Val Asp Ala Val Ala Asn Trp Tyr Phe Gly Asn Phe Leu
            100                 105                 110

Cys Lys Ala Val His Val Ile Tyr Thr Val Asn Leu Tyr Ser Ser Val
        115                 120                 125

Leu Ile Leu Ala Phe Ile Ser Leu Asp Arg Tyr Leu Ala Ile Val His
    130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                165                 170                 175

Ile Phe Ala Asn Val Ser Glu Ala Asp Asp Arg Tyr Ile Cys Asp Arg
            180                 185                 190

Phe Tyr Pro Asn Asp Leu Trp Val Val Val Phe Gln Phe Gln His Ile
        195                 200                 205

Met Val Gly Leu Ile Leu Pro Gly Ile Val Ile Leu Ser Cys Tyr Cys
    210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Ser Phe Ile Leu Leu Glu
            260                 265                 270

Ile Ile Lys Gln Gly Cys Glu Phe Glu Asn Thr Val His Lys Trp Ile
        275                 280                 285

Ser Ile Thr Glu Ala Leu Ala Phe Phe His Cys Cys Leu Asn Pro Ile
    290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335
```

```
Lys Arg Gly Gly His Ser Ser Val Ser Thr Glu Ser Glu Ser Ser Ser
            340                 345                 350

Phe His Ser Ser
        355
```

<210> SEQ ID NO 13
<211> LENGTH: 1071
<212> TYPE: DNA
<213> ORGANISM: Artificial Sequence
<220> FEATURE:
<223> OTHER INFORMATION: nucleotide sequence encoding CXCR4 Whim isoform I

<400> SEQUENCE: 13

```
atgtccattc ctttgcctct tttgcagata tacacttcag ataactacac cgaggaaatg     60

ggctcagggg actatgactc catgaaggaa ccctgtttcc gtgaagaaaa tgctaatttc    120

aataaaatct tcctgcccac catctactcc atcatcttct taactggcat tgtgggcaat    180

ggattggtca tcctggtcat gggttaccag aagaaactga gaagcatgac ggacaagtac    240

aggctgcacc tgtcagtggc cgacctcctc tttgtcatca cgcttccctt ctgggcagtt    300

gatgccgtgg caaactggta ctttgggaac ttcctatgca aggcagtcca tgtcatctac    360

acagtcaacc tctacagcag tgtcctcatc ctggccttca tcagtctgga ccgctacctg    420

gccatcgtcc acgccaccaa cagtcagagg ccaaggaagc tgttggctga aaaggtggtc    480

tatgttggcg tctggatccc tgccctcctg ctgactattc ccgacttcat ctttgccaac    540

gtcagtgagg cagatgacag atatatctgt gaccgcttct accccaatga cttgtgggtg    600

gttgtgttcc agtttcagca catcatggtt ggccttatcc tgcctggtat tgtcatcctg    660

tcctgctatt gcattatcat ctccaagctg tcacactcca agggccacca gaagcgcaag    720

gccctcaaga ccacagtcat cctcatcctg gctttcttcg cctgttggct gccttactac    780

attgggatca gcatcgactc cttcatcctc ctggaaatca tcaagcaagg gtgtgagttt    840

gagaacactg tgcacaagtg gatttccatc accgaggccc tagctttctt ccactgttgt    900

ctgaacccca tcctctatgc tttccttgga gccaaattta aaacctctgc ccagcacgca    960

ctcacctctg tgagcagagg gtccagcctc aagatcctct ccaaaggaaa gtgaggtgga   1020

cattcatctg tttccactga gtctgagtct tcaagttttc actccagcta a            1071
```

<210> SEQ ID NO 14
<211> LENGTH: 1071
<212> TYPE: DNA
<213> ORGANISM: Artificial Sequence
<220> FEATURE:
<223> OTHER INFORMATION: nucleotide sequence encoding CXCR4 Whim isoform I

<400> SEQUENCE: 14

```
atgtctattc ctctgcccct gctgcagatc tacaccagcg acaactacac cgaggaaatg     60

ggcagcggcg actacgacag catgaaggaa ccctgcttcc gggaagagaa cgccaacttc    120

aacaagatct tcctgcccac aatctacagc atcatctttc tgaccggcat cgtgggcaac    180

ggactcgtga tcctcgtgat gggctaccag aaaaagctgc ggagcatgac cgacaagtac    240

cggctgcacc tgagcgtggc cgacctgctg ttcgtgatca ccctgccttt ctgggccgtg    300

gacgccgtgg ccaattggta cttcggcaac ttcctgtgca aggccgtgca cgtgatctac    360

acagtgaacc tgtacagcag cgtgctgatc ctggccttca tcagcctgga cagatacctg    420
```

-continued

```
gccatcgtgc acgccaccaa cagccagcgg cctagaaagc tgctggccga gaaggtggtg    480

tacgtgggcg tgtggattcc cgccctgctg ctgaccatcc ccgacttcat cttcgccaac    540

gtgtccgagg ccgacgaccg gtacatctgc gaccggttct accccaacga cctgtgggtg    600

gtggtgttcc agttccagca catcatggtg ggactgatcc tgcctggcat cgtgattctg    660

agctgctact gcatcatcat cagcaagctg agccacagca agggccacca gaagcggaag    720

gccctgaaaa ccaccgtgat cctgattctg gctttcttcg cctgctggct gccctactac    780

atcggcatca gcatcgacag cttcatcctg ctggaaatca tcaagcaggg ctgcgagttc    840

gagaacaccg tgcacaagtg gatcagcatt accgaggccc tggccttttt ccactgctgc    900

ctgaacccta tcctgtacgc cttcctgggc gccaagttca agacctctgc ccagcacgcc    960

ctgaccagcg tgtccagagg aagcagcctg aagatcctga gcaagggcaa gtgaggcggc   1020

cacagctccg tgtctacaga gagcgagagc agcagcttcc acagcagctg a            1071
```

```
<210> SEQ ID NO 15
<211> LENGTH: 337
<212> TYPE: PRT
<213> ORGANISM: Artificial Sequence
<220> FEATURE:
<223> OTHER INFORMATION: CXCR4 Whim isoform I sequence

<400> SEQUENCE: 15

Met Ser Ile Pro Leu Pro Leu Leu Gln Ile Tyr Thr Ser Asp Asn Tyr
1               5                   10                  15

Thr Glu Glu Met Gly Ser Gly Asp Tyr Asp Ser Met Lys Glu Pro Cys
            20                  25                  30

Phe Arg Glu Glu Asn Ala Asn Phe Asn Lys Ile Phe Leu Pro Thr Ile
        35                  40                  45

Tyr Ser Ile Ile Phe Leu Thr Gly Ile Val Gly Asn Gly Leu Val Ile
    50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Ile Thr Leu Pro
                85                  90                  95

Phe Trp Ala Val Asp Ala Val Ala Asn Trp Tyr Phe Gly Asn Phe Leu
            100                 105                 110

Cys Lys Ala Val His Val Ile Tyr Thr Val Asn Leu Tyr Ser Ser Val
        115                 120                 125

Leu Ile Leu Ala Phe Ile Ser Leu Asp Arg Tyr Leu Ala Ile Val His
    130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                165                 170                 175

Ile Phe Ala Asn Val Ser Glu Ala Asp Asp Arg Tyr Ile Cys Asp Arg
            180                 185                 190

Phe Tyr Pro Asn Asp Leu Trp Val Val Val Phe Gln Phe Gln His Ile
        195                 200                 205

Met Val Gly Leu Ile Leu Pro Gly Ile Val Ile Leu Ser Cys Tyr Cys
    210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                245                 250                 255
```

```
Leu Pro Tyr Tyr Ile Gly Ile Ser Ile Asp Ser Phe Ile Leu Leu Glu
            260                 265                 270

Ile Ile Lys Gln Gly Cys Glu Phe Glu Asn Thr Val His Lys Trp Ile
        275                 280                 285

Ser Ile Thr Glu Ala Leu Ala Phe Phe His Cys Cys Leu Asn Pro Ile
    290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335

Lys


<210> SEQ ID NO 16
<211> LENGTH: 1059
<212> TYPE: DNA
<213> ORGANISM: Artificial Sequence
<220> FEATURE:
<223> OTHER INFORMATION: nucleotide sequence encoding CXCR4 Whim isoform
      II

<400> SEQUENCE: 16

atggagggga tcagtatata cacttcagat aactacaccg aggaaatggg ctcaggggac     60

tatgactcca tgaaggaacc ctgtttccgt gaagaaaatg ctaatttcaa taaaatcttc    120

ctgcccacca tctactccat catcttctta actggcattg tgggcaatgg attggtcatc    180

ctggtcatgg gttaccagaa gaaactgaga agcatgacgg acaagtacag gctgcacctg    240

tcagtggccg acctcctctt tgtcatcacg cttcccttct gggcagttga tgccgtggca    300

aactggtact ttgggaactt cctatgcaag gcagtccatg tcatctacac agtcaacctc    360

tacagcagtg tcctcatcct ggccttcatc agtctggacc gctacctggc catcgtccac    420

gccaccaaca gtcagaggcc aaggaagctg ttggctgaaa aggtggtcta tgttggcgtc    480

tggatccctg ccctcctgct gactattccc gacttcatct ttgccaacgt cagtgaggca    540

gatgacagat atatctgtga ccgcttctac cccaatgact tgtgggtggt tgtgttccag    600

tttcagcaca tcatggttgg ccttatcctg cctggtattg tcatcctgtc ctgctattgc    660

attatcatct ccaagctgtc acactccaag ggccaccaga agcgcaaggc cctcaagacc    720

acagtcatcc tcatcctggc tttcttcgcc tgttggctgc cttactacat tgggatcagc    780

atcgactcct tcatcctcct ggaaatcatc aagcaagggt gtgagtttga gaacactgtg    840

cacaagtgga tttccatcac cgaggcccta gctttcttcc actgttgtct gaaccccatc    900

ctctatgctt tccttggagc caaatttaaa acctctgccc agcacgcact cacctctgtg    960

agcagagggt ccagcctcaa gatcctctcc aaaggaaagt gaggtggaca ttcatctgtt   1020

tccactgagt ctgagtcttc aagttttcac tccagctaa                          1059


<210> SEQ ID NO 17
<211> LENGTH: 1059
<212> TYPE: DNA
<213> ORGANISM: Artificial Sequence
<220> FEATURE:
<223> OTHER INFORMATION: nucleotide sequence encoding CXCR4 Whim isoform
      II

<400> SEQUENCE: 17

atggaaggca tcagcatcta caccagcgac aactacaccg aggaaatggg cagcggcgac     60

tacgacagca tgaaggaacc ctgcttccgg gaagagaacg ccaacttcaa caagatcttc    120
```

```
ctgcccacaa tctacagcat catctttctg accggcatcg tgggcaacgg actcgtgatc    180

ctcgtgatgg gctaccagaa aaagctgcgg agcatgaccg acaagtaccg gctgcacctg    240

agcgtggccg acctgctgtt cgtgatcacc ctgcctttct gggccgtgga cgccgtggcc    300

aattggtact tcggcaactt cctgtgcaag gccgtgcacg tgatctacac agtgaacctg    360

tacagcagcg tgctgatcct ggccttcatc agcctggaca gatacctggc catcgtgcac    420

gccaccaaca gccagcggcc tagaaagctg ctggccgaga aggtggtgta cgtgggcgtg    480

tggattcccg ccctgctgct gaccatcccc gacttcatct tcgccaacgt gtccgaggcc    540

gacgaccggt acatctgcga ccggttctac cccaacgacc tgtgggtggt ggtgttccag    600

ttccagcaca tcatggtggg actgatcctg cctggcatcg tgattctgag ctgctactgc    660

atcatcatca gcaagctgag ccacagcaag ggccaccaga agcggaaggc cctgaaaacc    720

accgtgatcc tgattctggc tttcttcgcc tgctggctgc cctactacat cggcatcagc    780

atcgacagct tcatcctgct ggaaatcatc aagcagggct gcgagttcga gaacaccgtg    840

cacaagtgga tcagcattac cgaggccctg gcctttttcc actgctgcct gaaccctatc    900

ctgtacgcct tcctgggcgc caagttcaag acctctgccc agcacgccct gaccagcgtg    960

tccagaggaa gcagcctgaa gatcctgagc aagggcaagt gaggcggcca cagctccgtg   1020

tctacagaga gcgagagcag cagcttccac agcagctga                          1059
```

```
<210> SEQ ID NO 18
<211> LENGTH: 333
<212> TYPE: PRT
<213> ORGANISM: Artificial Sequence
<220> FEATURE:
<223> OTHER INFORMATION: CXCR4 Whim isoform II sequence

<400> SEQUENCE: 18

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190
```

-continued

```
Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys
                325                 330
```

COMPOSITIONS AND METHODS FOR HAEMATOPOIETIC STEM CELL TRANSPLANTATION

CROSS-REFERENCE TO RELATED APPLICATIONS

This application is a U.S. National Phase of International Patent Application No. PCT/EP2019/062666, filed on May 16, 2019, incorporated herein by reference, which claims priority benefit of United Kingdom Patent Application No. 1807944.2, filed on May 16, 2018.

INCORPORTATION OF INFORMATION SUBMITTED ELECTRONICALLY

Incorporated herein by reference in its entirety is a computer-readable sequence listing submitted as part of the application and identified as follows: name of ASCII text file: 56091_Seqlisting.txt; date of creation: Nov. 12, 2020; file size: 38,793 bytes. The specification is controlling in the event of any discrepancies between sequences in the specification and sequences in the electronic sequence listing.

FIELD OF THE INVENTION

The present invention relates to compositions and methods for haematopoietic stem cell transplantation. In particular, the invention relates to the genetic modification of haematopoietic stem and progenitor cells for improving their engraftment during transplantation.

BACKGROUND TO THE INVENTION

The haematopoietic system is a complex hierarchy of cells of different mature cell lineages. These include cells of the immune system that offer protection from pathogens, cells that carry oxygen through the body and cells involved in wound healing. All these mature cells are derived from a pool of haematopoietic stem cells (HSCs) that are capable of self-renewal and differentiation into any blood cell lineage. HSCs have the ability to replenish the entire haematopoietic system.

Haematopoietic cell transplantation (HCT) is a curative therapy for several inherited and acquired disorders. However, allogeneic HCT is limited by the poor availability of matched donors, the mortality associated with the allogeneic procedure which is mostly related to graft-versus-host disease (GvHD), and infectious complications provoked by the profound and long-lasting state of immune dysfunction.

Gene therapy approaches based on the transplantation of genetically modified autologous HSCs offer potentially improved safety and efficacy over allogeneic HCT. They are particularly relevant for patients lacking a matched donor.

The concept of stem cell gene therapy is based on the genetic modification of a relatively small number of stem cells. These persist long-term in the body by undergoing self-renewal, and generate large numbers of genetically "corrected" progeny. This can ensure a continuous supply of corrected cells for the rest of the patient's lifetime. HSCs are particularly attractive targets for gene therapy since their genetic modification will be passed to all blood cell lineages as they differentiate. Furthermore, HSCs can be easily and safely obtained, for example from bone marrow, mobilised peripheral blood and umbilical cord blood.

Efficient long-term gene modification of HSCs and their progeny benefits from technology which permits stable integration of the corrective DNA into the genome, without affecting HSC function. Accordingly, the use of integrating recombinant viral systems such as γ-retroviruses, lentiviruses and spumaviruses has dominated this field (Chang, A. H. et al. (2007) Mol. Ther. 15: 445-56). Therapeutic benefits have already been achieved in γ-retrovirus-based clinical trials for Adenosine Deaminase Severe Combined Immunodeficiency (ADA-SCID; Aiuti, A. et al. (2009) N. Engl. J. Med. 360: 447-58), X-linked Severe Combined Immunodeficiency (SCID-X1; Hacein-Bey-Abina, S. et al. (2010) N. Engl. J. Med. 363: 355-64) and Wiskott-Aldrich syndrome (WAS; Bortug, K. et al. (2010) N. Engl. J. Med. 363: 1918-27). In addition, lentiviruses have been employed as delivery vehicles in the treatment of X-linked adrenoleukodystrophy (ALD; Cartier, N. et al. (2009) Science 326: 818-23) and beta-thalassemia (Cartier, N. et al. (2010) Bull. Acad. Natl. Med. 194: 255-264; discussion 264-258), and recently for metachromatic leukodystrophy (MLD; Biffi, A. et al. (2013) Science 341: 1233158) and WAS (Aiuti, A. et al. (2013) Science 341: 1233151).

Furthermore, targeted gene editing has the potential to overcome possible issues associated with insertional mutagenesis and ectopic/unregulated transgene expression by allowing in situ correction of inherited mutations or targeted integration of transgene cassettes into safe genomic harbours.

However, current gene editing protocols based on homologous directed repair (HDR) still suffer from limited efficiency in HSCs, likely due to low expression of the HDR machinery, cell quiescence and limited uptake of template DNA. Because most gene therapy applications require substantial amounts of gene-edited HSCs, these limitations represent important hurdles that impact broader applicability of the technology and the safety of its clinical implementation. There is a significant need in the art to improve engraftment of the transplanted HSCs. In particular, there is a need to develop more efficient strategies to improve the ability of HSCs to home and permanently repopulate the recipient bone marrow (BM), especially when the number of cells in the graft is low.

Furthermore, both autologous and allogeneic HSPC transplantation typically require myeloablation through irradiation and/or chemotherapy in order to eradicate the subject's endogenous stem cell population prior to the infusion of HSPCs, and to suppress immune reactions. Unfortunately, these conditioning regimens are toxic for the subject short term (e.g. resulting in skin and gut toxicity, hair loss, diarrhoea, mucositis and multiple infections) and also long term (e.g. resulting in infertility, stunted skeletal and brain development and cancer). Thus, there is a further need for protocols that reduce genotoxic conditioning regimens before HSPC transplantation.

SUMMARY OF THE INVENTION

The inventors have developed a strategy to modify the expression and function of bone marrow-homing molecules to improve haematopoietic stem and/or progenitor cell engraftment.

The inventors have surprisingly found that overexpression of CD47 and/or C-X-C chemokine receptor type 4 (CXCR4) by HSPCs increases the efficiency of HSPC engraftment. In particular promoting increased homing after engraftment and repopulation of the recipient bone marrow.

In addition, the inventors have found that the CD47 and/or CXCR4 overexpressing HSPCs can be advantageously applied in transplantation protocols that utilise mild or no myeloablative conditioning.

For example, the inventors have found that the HSPCs are preferentially exchanged and/or selectively engrafted in subjects that have been subjected to mobilisation of their endogenous HSPCs. The transplanted HSPCs efficiently outcompete the endogenous HSPCs in repopulating the bone marrow.

Through testing these strategies in suitable haematochimeric models, the inventors believe they may increase the efficacy of conditioning regimens that bypass the requirement for toxic and mutagenic drugs (such as the endogenous HSPC mobilisation protocol disclosed above and conditioning regimens using HSPC-specific immunotoxins), thus reducing risk and long-term toxicity to the patient.

In one aspect the invention provides use of CD47 and/or C-X-C chemokine receptor type 4 (CXCR4) for increasing engraftment by haematopoietic stem and/or progenitor cells (HSPCs).

In one aspect the invention provides use of CD47 and/or C-X-C chemokine receptor type 4 (CXCR4) for increasing the capacity for engraftment by haematopoietic stem and/or progenitor cells (HSPCs).

The increased engraftment may be in comparison to natural HSPCs that have not been genetically engineered to express CD47 and/or CXCR4. Engraftment may be increased, for example, by at least about 10%, 20%, 30%, 40%, 50%, 75%, 100%, 200% or 500% in comparison to natural HSPCs that have not been genetically engineered to express CD47 and/or CXCR4.

In one embodiment, the use is an ex vivo use. In one embodiment, the use is an in vitro use.

In one embodiment, the HSPCs are genetically engineered to express the CD47 and/or CXCR4.

In another aspect the invention provides a method for increasing engraftment by haematopoietic stem and/or progenitor cells (HSPCs), wherein the method comprises the step of genetically engineering the HSPCs to express CD47 and/or C-X-C chemokine receptor type 4 (CXCR4).

In another aspect the invention provides a method for increasing engraftment by haematopoietic stem and/or progenitor cells (HSPCs), wherein the method comprises the step of transiently introducing CD47 and/or C-X-C chemokine receptor type 4 (CXCR4) into the HSPCs.

In another aspect the invention provides a method for increasing the capacity for engraftment by haematopoietic stem and/or progenitor cells (HSPCs), wherein the method comprises the step of genetically engineering the HSPCs to express CD47 and/or C-X-C chemokine receptor type 4 (CXCR4).

In another aspect the invention provides a method for increasing the capacity for engraftment by haematopoietic stem and/or progenitor cells (HSPCs), wherein the method comprises the step of transiently introducing CD47 and/or C-X-C chemokine receptor type 4 (CXCR4) into the HSPCs.

In one embodiment, the method is an ex vivo method. In one embodiment, the method is an in vitro method.

In one embodiment, the HSPCs are genetically engineered to express CD47. In one embodiment, the HSPCs are genetically engineered to express CXCR4. In a preferred embodiment, the HSPCs are genetically engineered to express CD47 and CXCR4.

In one embodiment, the HSPCs are transduced or transfected with one or more vectors encoding the CD47 and/or CXCR4.

In one embodiment, the HSPCs are transduced or transfected with a vector encoding the CD47. In one embodiment, the HSPCs are transduced or transfected with a vector encoding the CXCR4. In a preferred embodiment, the HSPCs are transduced or transfected with one or more vectors encoding the CD47 and CXCR4. The CD47 and CXCR4 may be, for example, encoded on separate vectors or on the same vector.

In one embodiment, the vector is a plasmid.

In one embodiment, the vector is a viral vector, for example a retroviral, adenoviral or adeno-associated viral vector. In one embodiment, the vector is a retroviral vector. In one embodiment, the vector is a lentiviral vector.

In a preferred embodiment, the expression of CD47 and/or CXCR4 is overexpression.

In one embodiment, the expression of CD47 and/or CXCR4 is stable expression. In a preferred embodiment, the expression of CD47 and/or CXCR4 is transient expression.

In a preferred embodiment, the CD47 is transiently expressed. In a preferred embodiment, the CXCR4 is transiently expressed. In a particularly preferred embodiment, the CD47 and CXCR4 are both transiently expressed.

In one embodiment, the HSPCs are transduced or transfected with one or more vectors encoding the CD47 and/or CXCR4, wherein the vectors are selected from the group consisting of RNA vectors, integration-defective lentiviral vectors (IDLVs), adeno-associated viral (AAV) vectors and Sendai viral vectors. For example, RNA encoding the CD47 and/or CXCR4 may be introduced into the HSPCs using RNA electroporation. Each of these may enable transient expression.

In one embodiment, the HSPCs are transduced or transfected with one or more vectors encoding the CD47 and/or CXCR4, wherein the vectors are RNA vectors. In one embodiment, the HSPCs are transduced or transfected with one or more vectors encoding the CD47 and/or CXCR4, wherein the vectors are Sendai viral vectors.

In one embodiment, CD47 and/or CXCR4 protein is directly introduced into the HSPCs, for example using protein electroporation. Direct protein introduction may enable CD47 and/or CXCR4 to be introduced transiently to HSPCs.

In one embodiment, the CD47 is human CD47.

In one embodiment, the CD47:

(a) is encoded by a nucleotide sequence that has at least 70% identity to SEQ ID NO: 8 or 1 (preferably SEQ ID NO: 8), preferably wherein the protein encoded by the nucleotide sequence substantially retains the natural function of the protein represented by any one of SEQ ID NOs: 2-5; and/or (b) comprises an amino acid sequence that has at least 70% identity to SEQ ID NO: 2-5, preferably wherein the amino acid sequence substantially retains the natural function of the protein represented by SEQ ID NOs: 2-5, respectively.

In one embodiment, the CXCR4 is human CXCR4.

In one embodiment, the CXCR4:

(a) is encoded by a nucleotide sequence that has at least 70% identity to SEQ ID NO: 9 or 6 (preferably SEQ ID NO: 9), preferably wherein the protein encoded by the nucleotide sequence substantially retains the natural function of the protein represented by SEQ ID NO: 7; and/or (b) comprises an amino acid sequence that has at least 70% identity to SEQ ID NO: 7, preferably wherein the amino acid sequence substantially retains the natural function of the protein represented by SEQ ID NO: 7.

In one embodiment, the CXCR4 is a truncated CXCR4. In one embodiment, the CXCR4 is a CXCR4 Whim isoform, optionally a CXCR4 Whim isoform I or a CXCR4 Whim isoform II.

In a preferred embodiment, the CXCR4 is encoded by a nucleotide sequence that has at least 70%, 80%, 90%, 95%, 96%, 97%, 98% 99% or 100% identity to SEQ ID NO: 14, preferably wherein the protein encoded by the nucleotide sequence substantially retains the natural function of the protein represented by SEQ ID NO: 15.

In one embodiment, the CD47 is a fusion with a destabilising domain protein. In one embodiment, the CXCR4 is a fusion with a destabilising domain protein. In one embodiment, the CD47 and CXCR4 are individually both fusions with destabilising domain proteins. Use of an example destabilising domain strategy is disclosed in Banaszynski et al. (2012) Cell. Typically, the transgene of interest (e.g. the CD47 and/or CXCR4) is operably linked to a destabilising domain protein (DD) that is tunable through the use of a stabilising agent (e.g. a small molecule). For example, the destabilising domain may be stable when bound to its stabilising agent, but may cause the fusion protein to be unstable in the absence thereof. For example, the CD47 and/or CXCR4 may be operably linked to a destabilising domain protein and delivered using a vector, such as a lentiviral Vector. The CD47 and/or CXCR4 in this form may be normally unstable, but expression of the CD47 and/or CXCR4 may then be induced (e.g. in vivo) for a time period of interest by the delivery of a stabilising agent. By "operably linked", it is to be understood that the individual components are linked together in a manner which enables them to carry out their function substantially unhindered.

In one embodiment, the HSPCs are further genetically engineered to express a transgene.

In one embodiment, the HSPCs are gene-edited. Gene editing may be achieved, for example, using one or more CRISPR/Cas systems, TALENs and/or zinc-finger nucleases. The gene editing may be, for example, to add a nucleic acid sequence (e.g. a transgene) at a specific target site or to delete a specific target nucleic acid sequence from the cells.

In one embodiment, the HSPCs are further transduced or transfected with one or more vectors encoding one or more transgenes.

In one embodiment, the HSPCs are mobilised peripheral blood HSPCs.

In a preferred embodiment, the CD47 and CXCR4 are both transiently expressed in mobilised peripheral blood HSPCs.

In another aspect the invention provides a population of genetically engineered haematopoietic stem and/or progenitor cells (HSPCs) obtainable by the method of the invention.

In another aspect the invention provides a population of genetically engineered haematopoietic stem and/or progenitor cells (HSPCs) which exhibit increased engraftment.

In another aspect the invention provides a population of genetically engineered haematopoietic stem and/or progenitor cells (HSPCs) which has an increased capacity for engraftment.

In another aspect the invention provides a population of genetically engineered haematopoietic stem and/or progenitor cells (HSPCs), wherein the HSPCs are genetically engineered to express CD47 and/or C-X-C chemokine receptor type 4 (CXCR4).

In one embodiment, the HSPCs are genetically engineered to express CD47. In one embodiment, the HSPCs are genetically engineered to express CXCR4. In a preferred embodiment, the HSPCs are genetically engineered to express CD47 and CXCR4.

In one embodiment, the HSPCs are transduced or transfected with one or more vectors encoding the CD47 and/or CXCR4.

In one embodiment, the HSPCs are transduced or transfected with a vector encoding the CD47. In one embodiment, the HSPCs are transduced or transfected with a vector encoding the CXCR4. In a preferred embodiment, the HSPCs are transduced or transfected with one or more vectors encoding the CD47 and CXCR4. The CD47 and CXCR4 may be, for example, encoded on separate vectors or on the same vector.

In one embodiment, the vector is a plasmid.

In one embodiment, the vector is a viral vector, for example a retroviral, adenoviral or adeno-associated viral vector. In one embodiment, the vector is a retroviral vector. In one embodiment, the vector is a lentiviral vector.

In a preferred embodiment, the expression of CD47 and/or CXCR4 is overexpression.

In one embodiment, the expression of CD47 and/or CXCR4 is stable expression. In a preferred embodiment, the expression of CD47 and/or CXCR4 is transient expression.

In a preferred embodiment, the CD47 is transiently expressed. In a preferred embodiment, the CXCR4 is transiently expressed. In a particularly preferred embodiment, the CD47 and CXCR4 are both transiently expressed.

In one embodiment, the HSPCs are transduced or transfected with one or more vectors encoding the CD47 and/or CXCR4, wherein the vectors are selected from the group consisting of RNA vectors, integration-defective lentiviral vectors (IDLVs), adeno-associated viral (AAV) vectors and Sendai viral vectors. For example, RNA encoding the CD47 and/or CXCR4 may be introduced into the HSPCs using RNA electroporation. Each of these may enable transient expression.

In one embodiment, the HSPCs are transduced or transfected with one or more vectors encoding the CD47 and/or CXCR4, wherein the vectors are RNA vectors. In one embodiment, the HSPCs are transduced or transfected with one or more vectors encoding the CD47 and/or CXCR4, wherein the vectors are Sendai viral vectors.

In one embodiment, CD47 and/or CXCR4 protein is directly introduced into the HSPCs, for example using protein electroporation. Direct protein introduction may enable CD47 and/or CXCR4 to be introduced transiently to HSPCs.

In one embodiment, the HSPCs are further genetically engineered to express a transgene.

In one embodiment, the HSPCs are gene-edited. Gene editing may be achieved, for example, using one or more CRISPR/Cas systems, TALENs and/or zinc-finger nucleases. The gene editing may be, for example, to add a nucleic acid sequence (e.g. a transgene) at a specific target site or to delete a specific target nucleic acid sequence from the cells.

In one embodiment, the HSPCs are transduced or transfected with one or more vectors encoding one or more transgenes.

In another aspect the invention provides a pharmaceutical composition comprising the population of genetically engineered haematopoietic stem and/or progenitor cells (HSPCs) of the invention and a pharmaceutically acceptable carrier, diluent or excipient.

In another aspect the invention provides a population of genetically engineered haematopoietic stem and/or progenitor cells (HSPCs) according to the invention for use in therapy.

In another aspect the invention provides a population of genetically engineered haematopoietic stem and/or progenitor cells (HSPCs) according to the invention for use in the treatment or prevention of cancer, an immune disorder, a lysosomal storage disorder, a bacterial or viral infection, a genetic disease, a blood disease, thalassemia or a sickle cell disease.

In another aspect the invention provides a method for haematopoietic stem and/or progenitor cell (HSPC) transplantation, comprising the steps:

(a) providing a population of HSPCs which are genetically engineered to express CD47 and/or C-X-C chemokine receptor type 4 (CXCR4); and
(b) administering the HSPCs to a subject.

In another aspect the invention provides a method of treating or preventing cancer, an immune disorder, a lysosomal storage disorder, a bacterial or viral infection, a genetic disease, a blood disease, thalassemia or a sickle cell disease, comprising the steps:

(a) providing a population of haematopoietic stem and/or progenitor cells (HSPCs) which are genetically engineered to express CD47 and/or C-X-C chemokine receptor type 4 (CXCR4); and
(b) administering the HSPCs to a subject.

In another aspect the invention provides a method for increasing engraftment by haematopoietic stem and/or progenitor cells (HSPCs), comprising the steps:

(a) providing a population of HSPCs which are genetically engineered to express CD47 and/or C-X-C chemokine receptor type 4 (CXCR4); and
(b) administering the HSPCs to a subject.

In one embodiment, the HSPCs are genetically engineered to express CD47. In one embodiment, the HSPCs are genetically engineered to express CXCR4. In a preferred embodiment, the HSPCs are genetically engineered to express CD47 and CXCR4.

In a one embodiment, the HSPCs are further genetically engineered to express a transgene. In another embodiment, the HSPCs are gene-edited.

In a preferred embodiment, the HSPCs are further genetically engineered to express a transgene, wherein the transgene is inserted into the HSPCs using gene editing. The gene editing may enable insertion of the transgene at a specific target site in the HSPCs, for example using one or more CRISPR/Cas systems, TALENs and/or zinc-finger nucleases.

In one embodiment, the HSPCs are administered as part of an autologous stem cell transplant procedure.

In one embodiment, the HSPCs are administered as part of an allogeneic stem cell transplant procedure.

In one embodiment, the subject is subjected to a mild myeloablative conditioning regimen before administration of the HSPCs.

In one embodiment, the subject is subjected to a reduced intensity conditioning regimen before administration of the HSPCs.

In one embodiment, the subject is subjected to a non-myeloablative conditioning regimen before administration of the HSPCs.

In one embodiment, the subject is subjected to a regimen for mobilisation of endogenous HSPCs. Preferably, the regimen for mobilisation of endogenous HSPCs is administered before administration of the HSPCs.

In one embodiment, the subject is administered one or more HSPC mobilisation agents before administration of the HSPCs.

In one embodiment, the subject is administered granulocyte colony stimulating factor (GCSF), Plerixafor and/or BIO5192 before administration of the HSPCs. In one embodiment, the subject is administered GROβ (GROβΔ4/CXCL2Δ4) and Plerixafor before administration of the HSPCs. Preferably, the HSPCs are genetically engineered to express CXCR4, or CD47 and CXCR4.

In one embodiment, the subject subjected to conditioning with one or more HSPC-specific immunotoxins. Preferably, the one or more HSPC-specific immunotoxins are administered before administration of the HSPCs.

In one embodiment, the subject is administered an antibody conjugated to a toxin before administration of the HSPCs.

Preferably, the HSPCs are administered to the subject after the toxin has dissipated from the bone marrow of the subject.

In one embodiment, the subject does not undergo chemotherapy or radiotherapy conditioning before administration of the HSPCs.

Figure 1:
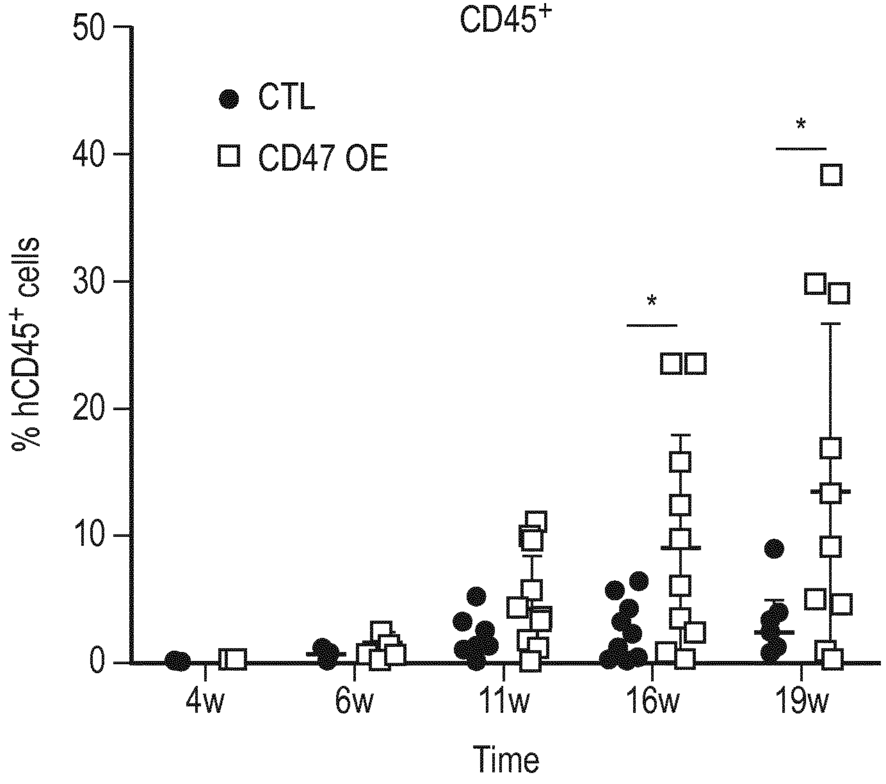
FIG. 1
Figure 1:
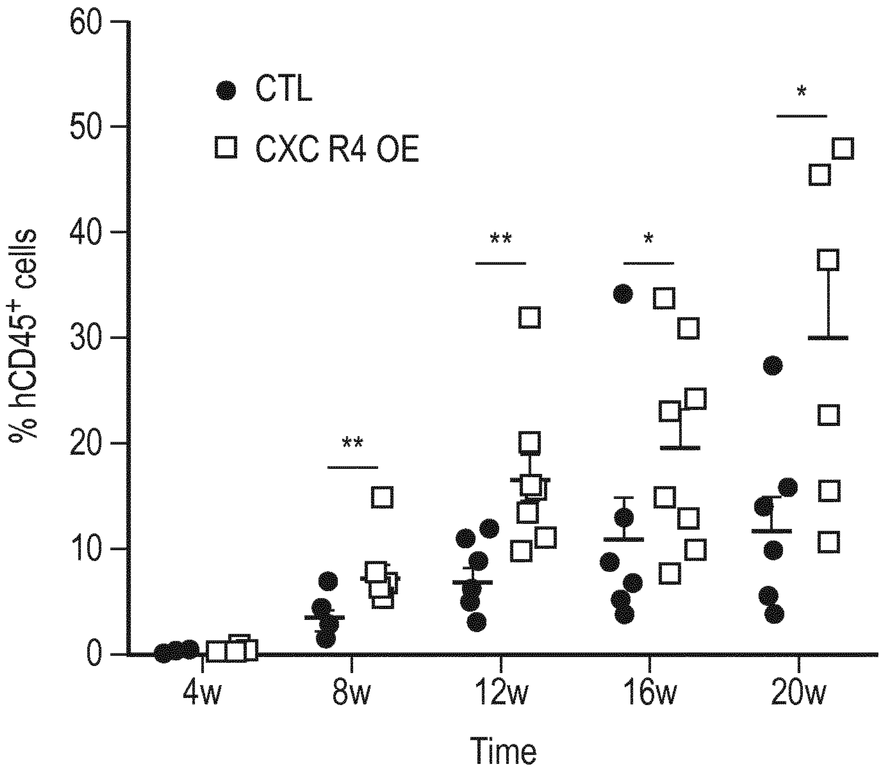
Figure 1:
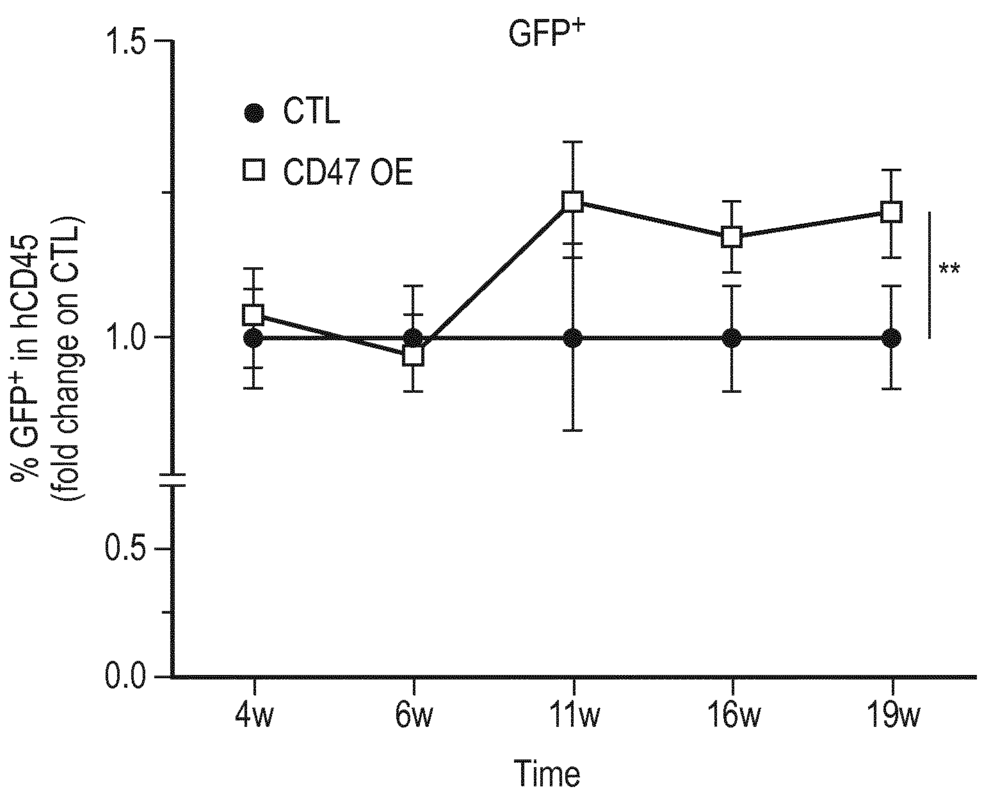
Figure 1:
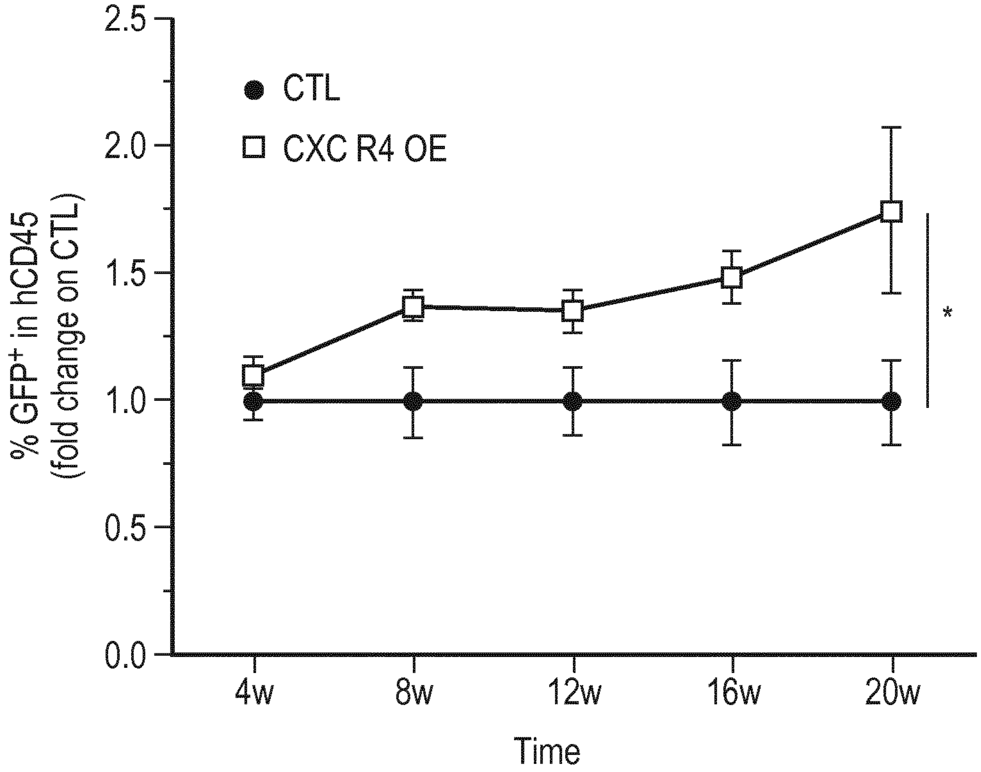
Figure 1:
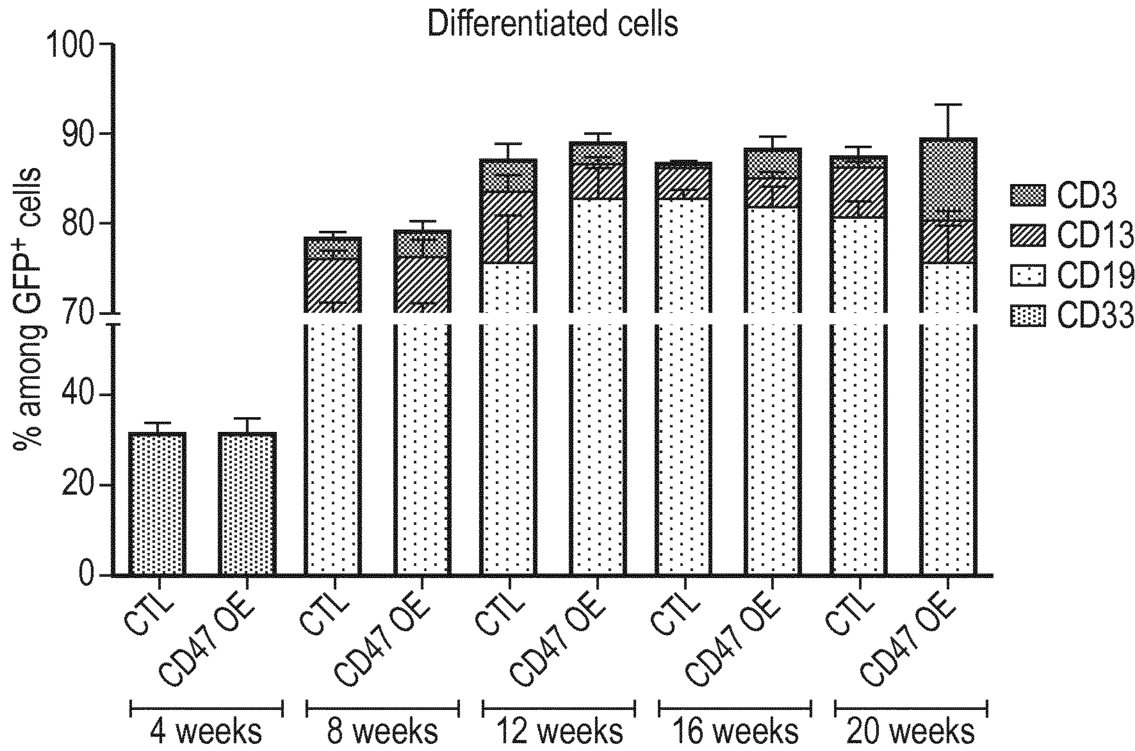
Figure 1:
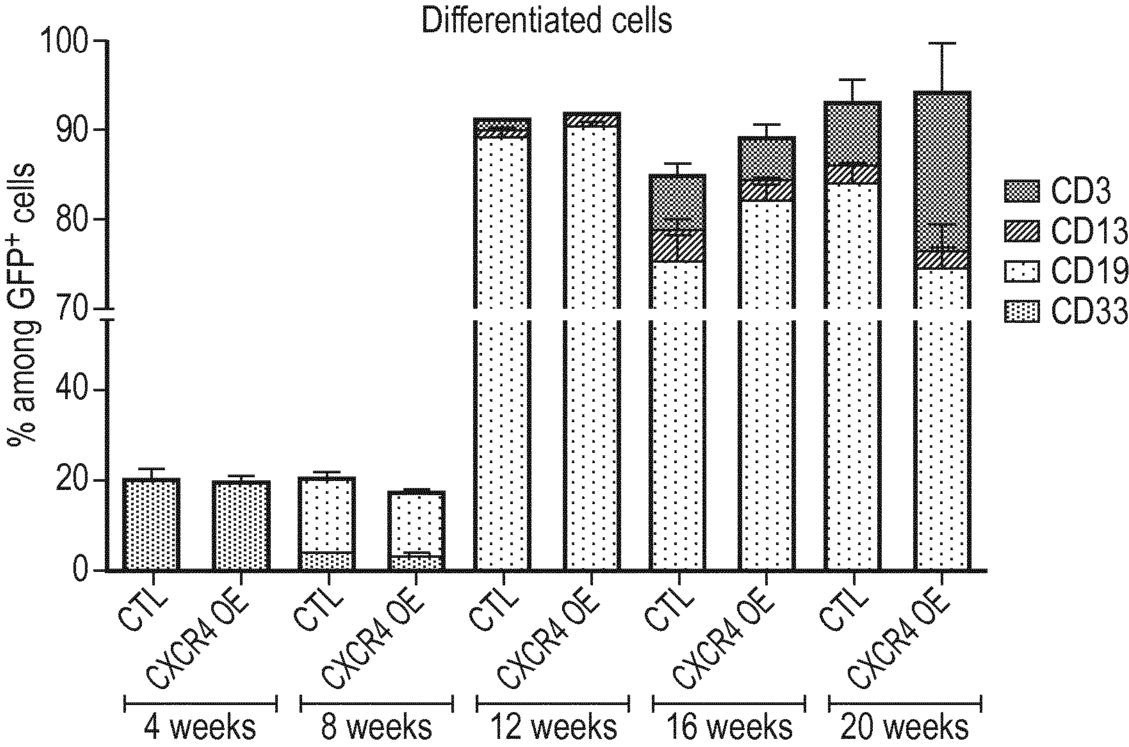

In vivo engraftment of CD34+ cells that constitutively overexpress (OE) CD47 or CXCR4. Cord blood CD34+ cells were transduced with a bi-directional lentivirus allowing stable overexpression of CD47-GFP or CXCR4-GFP. Cells were engrafted in immune-compromised NSG mice. Levels of engraftment were evaluated by following human CD45+ cell % within peripheral blood (left panel). Engraftment was higher in both cases, with an increase in GFP+ cell population (middle panel), without affecting long term haematopoiesis (right panel).

FIG. 2

Transient overexpression of CD47 and CXCR4 in gene edited cells. Cord Blood CD34+ cells were gene edited in vitro and electroporated with CD47, CXCR4 or both (mix) mRNA. The left panel show the transient overexpression of both targets. The right panel shows efficient gene editing (GFP gene insertion in the AAVS1 locus) in the different conditions. AAV-alone and $H_2O$ serve as negative control, GE (gene-edited only) serves as positive control.

FIG. 3

In vivo engraftment of gene-edited (GE) CD34+CD38− cells that transiently overexpress CD47 and/or CXCR4. Gene edited cord blood CD34+CD38− primitive cells were electroporated with CD47 and/or CXCR4 RNA. Level of engraftment was evaluated by following human CD45+ cell % within peripheral blood. Transient overexpression of CD47 alone or in combination with CXCR4 (mix group) shows a long-term increased engraftment advantage (left panel, purple and orange) compared to the control group (GFP, green). Gene-edited cells (GFP+) were also selectively advantaged (right panel, purple and orange).

FIG. 4

In vivo validation of mobilisation protocol. NSG mice were stably engrafted with cord blood CD34+ cells. After 5 weeks, mice were treated with mobilisation drugs (GCSF 250 μg/kg/day for 7 days with osmotic pumps; Plerixafor 5 mg/kg/day and BIO5192 1 mg/kg/day the last two days by IP injections). The mobilisation protocol was validated in vivo as we obtained a 5-fold increase in circulated progenitors CD34+CD38− (left panel). As an internal control, we followed murine stem cells (Kit+, Lin−, Sca1+, KLS) that were observed at 142-fold higher levels in peripheral circulation after treatment (middle panel). Plerixafor being the specific antagonist of CXCR4, CXCR4 expression was followed at the surface of human CD45+ cells and is significantly overexpressed after mobilisation treatment (right panel).

FIG. 5

HSC mobilisation from the bone marrow and CXCR4 overexpressing cell recolonisation. NSG mice stably engrafted with bone marrow derived CD34+ were treated for mobilisation (GCSF 250 μg/kg/day for 7 days with osmotic pumps; Plerixafor 5 mg/kg/day and BIO5192 1 mg/kg/day the last two days by IP injections) and then infused with bone marrow CD34+ cells overexpressing CXCR4-GFP or gene marked control (CTL-GFP) from the same donor. % of human CD45+ cell engraftment was followed in peripheral blood (left panel). GFP+ marked cells, from the second engraftment, were followed and CXCR4 overexpressing cells efficiently engrafted compare to control (CTL) (middle panel, 7-9% vs 1-2%) without impacting long term haematopoiesis (right panel).

FIG. 6

In vitro evaluation of transient CXCR4 and CD47 overexpression (OE) in mobilised Peripheral Blood (mPB). mPB CD34+ cells were nucleofected with mRNA coding for CXCR4 and CD47 and their expression levels were evaluated over time. These cells show up to 6 fold increase of expression as compared to their basal levels.

FIG. 7

In vivo engraftment of mPB CD34+ cells that transiently overexpress CD47 and CXCR4. mPB CD34+ cells were nucleofected with mRNA coding for CXCR4 and CD47 allowing transient overexpression of the genes of interest. Cells were engrafted in NSG mice. Levels of engraftment were evaluated by following human CD45+ cell % within peripheral blood (top-left panel). Engraftment was higher without significantly affecting lineage reconstitution at long term (top-right panel). Engraftment capacity was evaluated in the bone marrow 13 weeks after transplantation. Engraftment was higher (bottom-left panel) and no differences were identified in the most stem cell compartment (bottom-right panel).

FIG. 8

In vivo confirmation of mobilisation protocol on mPB CD34+ cells in NSGW41 mice. NSGW41 mice were stably engrafted with mPB CD34+ cells. After 8 weeks, mice were treated with mobilisation drugs (GCSF 250 μg/kg/day for 7 days with osmotic pumps; Plerixafor 5 mg/kg/day and BIO5192 1 mg/kg/day the last two days by IP injections). The mobilisation protocol was confirmed in vivo as we obtained a 3-fold increase of total white blood cells in circulation (left panel); a 2-fold increase in circulated progenitors CD34+CD38− (right panel). As an internal control, we followed murine stem cells (Kit+, Lin−, Sca1+, KLS) that were observed at 25-fold higher levels in peripheral circulation after treatment (middle panel).

FIG. 9

HSC mobilisation from bone marrow and CXCR4+CD47 transiently overexpressing cell recolonisation. NSGW41 mice stably engrafted with mPB CD34+ cells were treated for mobilisation and then infused with stably expressing GFP+ mPB cells coming from the same donor transiently overexpressing CXCR4 and CD47 or mRNA coding for GFP as a control (top scheme). % of human CD45+ cell engraftment was followed in peripheral blood (left panel). GFP+ marked cells, from the second engraftment, were followed and CXCR4+CD47 overexpressing cells engrafted better than the control counterpart, especially at late time point (middle panel). These results were confirmed also by looking at the absolute count of the GFP+ cells (right panel).

FIG. 10

In vitro evaluation of CXCR4 Whim isoform I functionality versus Wild-Type (Wt) isoform I counterpart and the control (GFP). Cord Blood CD34+ cells were nucleofected with mRNA coding for CXCR4 Wt isoform I or CXCR4 Whim isoform I allowing transient overexpression of the genes of interest. One day after culture the levels of CXCR4 expression were evaluated (left panel) and a migration assay was performed. 30 minutes after incubation, the number of migrating cells (in the lower chamber) was evaluated (right panel).

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

In one aspect the invention provides use of CD47 and/or C-X-C chemokine receptor type 4 (CXCR4) for increasing engraftment by haematopoietic stem and/or progenitor cells (HSPCs).

In another aspect the invention provides a method for increasing engraftment by haematopoietic stem and/or progenitor cells (HSPCs), wherein the method comprises the step of genetically engineering the HSPCs to express CD47 and/or C-X-C chemokine receptor type 4 (CXCR4).

In one embodiment, the HSPCs are genetically engineered to express CD47. In one embodiment, the HSPCs are genetically engineered to express CXCR4. In a preferred embodiment, the HSPCs are genetically engineered to express CD47 and CXCR4.

The term "genetically engineered" as used herein refers to the manipulation of a precursor cell, for example a natural cell, by the introduction of exogenous genetic material. Accordingly, in the context of the present invention a HSPC may be genetically engineered by the introduction of genetic material that encodes and enables the expression of exogenous CD47 and/or CXCR4 by the cell.

Cluster of Differentiation 47 (CD47)

Cluster of differentiation 47 (CD47; also known as integrin-associated protein, IAP) is a transmembrane protein belonging to the immunoglobulin superfamily. CD47 binds thrombospondin-1 (TSP-1) and signal-regulatory protein alpha (SIRPα), and functions as a signal to macrophages.

In a preferred embodiment, the CD47 is human CD47.

In a preferred embodiment, the nucleotide sequence encoding the CD47 is codon optimised.

In one embodiment, the nucleotide sequence encoding CD47 is:

```
                                            (SEQ ID NO: 8)
ATGTGGCCTCTCGTGGCCGCTCTGCTGCTCGGGAGCGCTTGTTGCGGCAG

CGCCCAGCTGCTGTTCAACAAAACCAAGTCCGTCGAGTTCACCTTCTGCA

ACGACACAGTGGTGATCCCCTGCTTCGTCACCAACATGGAGGCTCAGAAT
```

-continued

```
ACCACCGAGGTCTACGTCAAGTGGAAATTCAAGGGCAGAGACATCTACAC
CTTCGACGGAGCCCTCAACAAGAGCACAGTGCCTACCGACTTTTCCAGCG
CCAAGATTGAGGTGAGCCAACTCCTGAAGGGAGACGCCAGCCTGAAGATG
GACAAGAGCGATGCCGTCAGCCACACAGGAAACTACACCTGCGAGGTGAC
AGAGCTCACCAGAGAGGGCGAGACCATCATCGAGCTCAAATACAGAGTGG
TGTCCTGGTTCTCCCCCAACGAGAACATCCTCATCGTGATCTTCCCCATC
TTCGCCATCCTGCTGTTCTGGGGCCAGTTCGGCATCAAAACCCTGAAGTA
TAGATCCGGCGGCATGGACGAGAAAACAATCGCCCTGCTGGTGGCCGGCC
TCGTGATTACCGTGATCGTCATCGTGGGCGCCATCCTCTTCGTGCCCGGA
GAGTACAGCCTCAAGAACGCCACCGGCCTGGGCCTGATTGTGACCTCCAC
AGGCATTCTGATCCTGCTGCACTACTACGTGTTCAGCACAGCCATTGGCC
TCACAAGCTTCGTGATCGCCATCCTGGTCATCCAGGTGATCGCCTACATC
CTCGCCGTGGTCGGACTCAGCCTCTGTATTGCCGCTTGCATCCCCATGCA
CGGACCCCTCCTGATCTCCGGCCTCAGCATTCTGGCTCTCGCTCAGCTGC
TCGGCCTGGTGTACATGAAGTTCGTCGCCAGCAACCAGAAGACCATCCAA
CCCCCCAGAAAGGCCGTCGAAGAGCCTCTGAACGCCTTTAAGGAGAGCAA
GGGCATGATGAACGACGAG
```

In another embodiment, the nucleotide sequence encoding CD47 is:

```
                                         (SEQ ID NO: 1)
ATGTGGCCCCTGGTAGCGGCGCTGTTGCTGGGCTCGGCGTGCTGCGGATC
AGCTCAGCTACTATTTAATAAAACAAAATCTGTAGAATTCACGTTTTGTA
ATGACACTGTCGTCATTCCATGCTTTGTTACTAATATGGAGGCACAAAAC
ACTACTGAAGTATACGTAAAGTGGAAATTTAAAGGAAGAGATATTTACAC
CTTTGATGGAGCTCTAAACAAGTCCACTGTCCCCACTGACTTTAGTAGTG
CAAAAATTGAAGTCTCACAATTACTAAAAGGAGATGCCTCTTTGAAGATG
GATAAGAGTGATGCTGTCTCACACACAGGAAACTACACTTGTGAAGTAAC
AGAATTAACCAGAGAAGGTGAAACGATCATCGAGCTAAAATATCGTGTTG
TTTCATGGTTTTCTCCAAATGAAAATATTCTTATTGTTATTTTCCCAATT
TTTGCTATACTCCTGTTCTGGGGACAGTTTGGTATTAAAACACTTAAATA
TAGATCCGGTGGTATGGATGAGAAAACAATTGCTTTACTTGTTGCTGGAC
TAGTGATCACTGTCATTGTCATTGTTGGAGCCATTCTTTTCGTCCCAGGT
GAATATTCATTAAAGAATGCTACTGGCCTTGGTTTAATTGTGACTTCTAC
AGGGATATTAATATTACTTCACTACTATGTGTTTAGTACAGCGATTGGAT
TAACCTCCTTCGTCATTGCCATATTGGTTATTCAGGTGATAGCCTATATC
CTCGCTGTGGTTGGACTGAGTCTCTGTATTGCGGCGTGTATACCAATGCA
TGGCCCTCTTCTGATTTCAGGTTTGAGTATCTTAGCTCTAGCACAATTAC
TTGGACTAGTTTATATGAAATTTGTGGCTTCCAATCAGAAGACTATACAA
CCTCCTAGGAAAGCTGTAGAGGAACCCCTTAATGCATTCAAAGAATCAAA
AGGAATGATGAATGATGAATAA
```

In one embodiment, the amino acid sequence of CD47 is:

```
                                         (SEQ ID NO: 2)
MWPLVAALLLGSACCGSAQLLFNKTKSVEFTFCNDTVVIPCFVTNMEAQN
TTEVYVKWKFKGRDIYTFDGALNKSTVPTDFSSAKIEVSQLLKGDASLKM
DKSDAVSHTGNYTCEVTELTREGETIIELKYRVVSWFSPNENILIVIFFI
FAILLFWGQFGIKTLKYRSGGMDEKTIALLVAGLVITVIVIVGAILFVFG
EYSLKNATGLGLIVTSTGILILLHYYVFSTAIGLTSFVIAILVIQVIAYI
LAVVGLSLCIAACIPMHGPLLISGLSILALAQLLGLVYMKFVASNQKTIQ
PPRKAVEEPLNAFKESKGMMNDE
```

In another embodiment, the amino acid sequence of CD47 is:

```
                                         (SEQ ID NO: 3)
MWPLVAALLLGSACCGSAQLLFNKTKSVEFTFCNDTVVIPCFVTNMEA
QNTTEVYVKWKFKGRDIYTFDGALNKSTVPTDFSSAKIEVSQLLKGDA
SLKMDKSDAVSHTGNYTCEVTELTREGETIIELKYRVVSWFSPNENIL
IVIFPIFAILLFWGQFGIKTLKYRSGGMDEKTIALLVAGLVITVIVIV
GAILFVPGEYSLKNATGLGLIVTSTGILILLHYYVFSTAIGLTSFVIA
ILVIQVIAYILAVVGLSLCIAACIPMHGPLLISGLSILALAQLLGLVY
MKFV
```

In another embodiment, the amino acid sequence of CD47 is:

```
                                         (SEQ ID NO: 4)
MWPLVAALLLGSACCGSAQLLFNKTKSVEFTFCNDTVVIPCFVTNMEA
QNTTEVYVKWKFKGRDIYTFDGALNKSTVPTDFSSAKIEVSQLLKGDA
SLKMDKSDAVSHTGNYTCEVTELTREGETIIELKYRVVSWFSPNENIL
IVIFFIFAILLFWGQFGIKTLKYRSGGMDEKTIALLVAGLVITVIVIV
GAILFVFGEYSLKNATGLGLIVTSTGILILLHYYVFSTAIGLTSFVIA
ILVIQVIAYILAVVGLSLCIAACIPMHGPLLISGLSILALAQLLGLVY
MKFVASNQKTIQPPRNN
```

In another embodiment, the amino acid sequence of CD47 is:

```
                                         (SEQ ID NO: 5)
MWPLVAALLLGSACCGSAQLLFNKTKSVEFTFCNDTVVIPCFVTNMEA
QNTTEVYVKWKFKGRDIYTFDGALNKSTVPTDFSSAKIEVSQLLKGDA
SLKMDKSDAVSHTGNYTCEVTELTREGETIIELKYRVVSWFSPNENIL
IVIFPIFAILLFWGQFGIKTLKYRSGGMDEKTIALLVAGLVITVIVIV
GAILFVPGEYSLKNATGLGLIVTSTGILILLHYYVFSTAIGLTSFVIA
ILVIQVIAYILAVVGLSLCIAACIPMHGPLLISGLSILALAQLLGLVY
MKFVASNQKTIQPPRKAVEEPLN
```

In one embodiment, the CD47 is encoded by a nucleotide sequence that has at least 70%, 80%, 90%, 95%, 96%, 97%, 98% 99% or 100% identity to SEQ ID NO: 8 or 1 (preferably SEQ ID NO: 8), preferably wherein the protein encoded by the nucleotide sequence substantially retains the natural function of the protein represented by any one of SEQ ID NOs: 2-5.

In one embodiment, the CD47 is encoded by a nucleotide sequence that encodes an amino acid sequence that has at least 70%, 80%, 90%, 95%, 96%, 97%, 98% 99% or 100% identity to SEQ ID NO: 2-5, preferably wherein the amino acid sequence substantially retains the natural function of the protein represented by SEQ ID NOs: 2-5, respectively.

In one embodiment, the CD47 comprises or consists of an amino acid sequence that has at least 70%, 80%, 90%, 95%, 96%, 97%, 98% 99% or 100% identity to SEQ ID NO: 2-5, preferably wherein the amino acid sequence substantially retains the natural function of the protein represented by SEQ ID NOs: 2-5, respectively.

C-X-C Chemokine Receptor Type 4 (CXCR4)

C-X-C chemokine receptor type 4 (CXCR4) is a receptor expressed on the surface of HSPCs. The interaction of CXCR4 with CXCL12 is one of the major mechanisms that directs migration to the bone marrow.

CXCR4 may also known as fusin or CD184.

In a preferred embodiment, the CXCR4 is human CXCR4.

In a preferred embodiment, the nucleotide sequence encoding the CXCR4 is codon optimised.

In one embodiment, the nucleotide sequence encoding CXCR4 is:

```
                                         (SEQ ID NO: 9)
ATGTCTATTCCTCTGCCCCTGCTGCAGATCTACACCAGCGACAACTAC

ACCGAGGAAATGGGCAGCGGCGACTACGACAGCATGAAGGAACCCTGC

TTCCGGGAAGAGAACGCCAACTTCAACAAGATCTTCCTGCCCACAATC

TACAGCATCATCTTTCTGACCGGCATCGTGGGCAACGGACTCGTGATC

CTCGTGATGGGCTACCAGAAAAAGCTGCGGAGCATGACCGACAAGTAC

CGGCTGCACCTGAGCGTGGCCGACCTGCTGTTCGTGATCACCCTGCCT

TTCTGGGCCGTGGACGCCGTGGCCAATTGGTACTTCGGCAACTTCCTG

TGCAAGGCCGTGCACGTGATCTACACAGTGAACCTGTACAGCAGCGTG

CTGATCCTGGCCTTCATCAGCCTGGACAGATACCTGGCCATCGTGCAC

GCCACCAACAGCCAGCGGCCTAGAAAGCTGCTGGCCGAGAAGGTGGTG

TACGTGGGCGTGTGGATTCCCGCCCTGCTGCTGACCATCCCCGACTTC

ATCTTCGCCAACGTGTCCGAGGCCGACGACCGGTACATCTGCGACCGG

TTCTACCCCAACGACCTGTGGGTGGTGGTGTTCCAGTTCCAGCACATC

ATGGTGGGACTGATCCTGCCTGGCATCGTGATTCTGAGCTGCTACTGC

ATCATCATCAGCAAGCTGAGCCACAGCAAGGGCCACCAGAAGCGGAAG

GCCCTGAAAACCACCGTGATCCTGATTCTGGCTTTCTTCGCCTGCTGG

CTGCCCTACTACATCGGCATCAGCATCGACAGCTTCATCCTGCTGGAA

ATCATCAAGCAGGGCTGCGAGTTCGAGAACACCGTGCACAAGTGGATC

AGCATTACCGAGGCCCTGGCCTTTTTCCACTGCTGCCTGAACCCTATC

CTGTACGCCTTCCTGGGCGCCAAGTTCAAGACCTCTGCCCAGCACGCC

CTGACCAGCGTGTCCAGAGGAAGCAGCCTGAAGATCCTGAGCAAGGGC

AAGAGAGGCGGCCACAGCTCCGTGTCTACAGAGAGCGAGAGCAGCAGC

TTCCACAGCAGCTGA
```

In another embodiment, the nucleotide sequence encoding CXCR4 is:

```
                                        (SEQ ID NO: 10)
ATGTCCATTCCTTTGCCTCTTTTGCAGATATACACTTCAGATAACTAC

ACCGAGGAAATGGGCTCAGGGGACTATGACTCCATGAAGGAACCCTGT

TTCCGTGAAGAAAATGCTAATTTCAATAAAATCTTCCTGCCCACCATC

TACTCCATCATCTTCTTAACTGGCATTGTGGGCAATGGATTGGTCATC

CTGGTCATGGGTTACCAGAAGAAACTGAGAAGCATGACGGACAAGTAC

AGGCTGCACCTGTCAGTGGCCGACCTCCTCTTTGTCATCACGCTTCCC

TTCTGGGCAGTTGATGCCGTGGCAAACTGGTACTTTGGGAACTTCCTA

TGCAAGGCAGTCCATGTCATCTACACAGTCAACCTCTACAGCAGTGTC

CTCATCCTGGCCTTCATCAGTCTGGACCGCTACCTGGCCATCGTCCAC

GCCACCAACAGTCAGAGGCCAAGGAAGCTGTTGGCTGAAAAGGTGGTC

TATGTTGGCGTCTGGATCCCTGCCCTCCTGCTGACTATTCCCGACTTC

ATCTTTGCCAACGTCAGTGAGGCAGATGACAGATATATCTGTGACCGC

TTCTACCCCAATGACTTGTGGGTGGTTGTGTTCCAGTTTCAGCACATC

ATGGTTGGCCTTATCCTGCCTGGTATTGTCATCCTGTCCTGCTATTGC

ATTATCATCTCCAAGCTGTCACACTCCAAGGGCCACCAGAAGCGCAAG

GCCCTCAAGACCACAGTCATCCTCATCCTGGCTTTCTTCGCCTGTTGG

CTGCCTTACTACATTGGGATCAGCATCGACTCCTTCATCCTCCTGGAA

ATCATCAAGCAAGGGTGTGAGTTTGAGAACACTGTGCACAAGTGGATT

TCCATCACCGAGGCCCTAGCTTTCTTCCACTGTTGTCTGAACCCCATC

CTCTATGCTTTCCTTGGAGCCAAATTTAAAACCTCTGCCCAGCACGCA

CTCACCTCTGTGAGCAGAGGGTCCAGCCTCAAGATCCTCTCCAAAGGA

AAGCGAGGTGGACATTCATCTGTTTCCACTGAGTCTGAGTCTTCAAGT

TTTCACTCCAGCTAA
```

In another embodiment, the nucleotide sequence encoding CXCR4 is:

```
                                        (SEQ ID NO: 11)
ATGGAAGGCATCAGCATCTACACCAGCGACAACTACACCGAGGAAATG

GGCAGCGGCGACTACGACAGCATGAAGGAACCCTGCTTCCGGGAAGAG

AACGCCAACTTCAACAAGATCTTCCTGCCCACAATCTACAGCATCATC

TTTCTGACCGGCATCGTGGGCAACGGACTCGTGATCCTCGTGATGGGC

TACCAGAAAAAGCTGCGGAGCATGACCGACAAGTACCGGCTGCACCTG

AGCGTGGCCGACCTGCTGTTCGTGATCACCCTGCCTTTCTGGGCCGTG

GACGCCGTGGCCAATTGGTACTTCGGCAACTTCCTGTGCAAGGCCGTG

CACGTGATCTACACAGTGAACCTGTACAGCAGCGTGCTGATCCTGGCC

TTCATCAGCCTGGACAGATACCTGGCCATCGTGCACGCCACCAACAGC

CAGCGGCCTAGAAAGCTGCTGGCCGAGAAGGTGGTGTACGTGGGCGTG

TGGATTCCCGCCCTGCTGCTGACCATCCCCGACTTCATCTTCGCCAAC

GTGTCCGAGGCCGACGACCGGTACATCTGCGACCGGTTCTACCCCAAC
```

-continued

```
GACCTGTGGGTGGTGGTGTTCCAGTTCCAGCACATCATGGTGGGACTG
ATCCTGCCTGGCATCGTGATTCTGAGCTGCTACTGCATCATCATCAGC
AAGCTGAGCCACAGCAAGGGCCACCAGAAGCGGAAGGCCCTGAAAACC
ACCGTGATCCTGATTCTGGCTTTCTTCGCCTGCTGGCTGCCCTACTAC
ATCGGCATCAGCATCGACAGCTTCATCCTGCTGGAAATCATCAAGCAG
GGCTGCGAGTTCGAGAACACCGTGCACAAGTGGATCAGCATTACCGAG
GCCCTGGCCTTTTTCCACTGCTGCCTGAACCCTATCCTGTACGCCTTC
CTGGGCGCCAAGTTCAAGACCTCTGCCCAGCACGCCCTGACCAGCGTG
TCCAGAGGAAGCAGCCTGAAGATCCTGAGCAAGGGCAAGAGAGGCGGC
CACAGCTCCGTGTCTACAGAGAGCGAGAGCAGCAGCTTCCACAGCAGC
TGA
```

In another embodiment, the nucleotide sequence encoding CXCR4 is:

(SEQ ID NO: 6)

```
ATGGAGGGGATCAGTATATACACTTCAGATAACTACACCGAGGAAATG
GGCTCAGGGGACTATGACTCCATGAAGGAACCCTGTTTCCGTGAAGAA
AATGCTAATTTCAATAAAATCTTCCTGCCCACCATCTACTCCATCATC
TTCTTAACTGGCATTGTGGGCAATGGATTGGTCATCCTGGTCATGGGT
TACCAGAAGAAACTGAGAAGCATGACGGACAAGTACAGGCTGCACCTG
TCAGTGGCCGACCTCCTCTTTGTCATCACGCTTCCCTTCTGGGCAGTT
GATGCCGTGGCAAACTGGTACTTTGGGAACTTCCTATGCAAGGCAGTC
CATGTCATCTACACAGTCAACCTCTACAGCAGTGTCCTCATCCTGGCC
TTCATCAGTCTGGACCGCTACCTGGCCATCGTCCACGCCACCAACAGT
CAGAGGCCAAGGAAGCTGTTGGCTGAAAAGGTGGTCTATGTTGGCGTC
TGGATCCCTGCCCTCCTGCTGACTATTCCCGACTTCATCTTTGCCAAC
GTCAGTGAGGCAGATGACAGATATATCTGTGACCGCTTCTACCCCAAT
GACTTGTGGGTGGTTGTGTTCCAGTTTCAGCACATCATGGTTGGCCTT
ATCCTGCCTGGTATTGTCATCCTGTCCTGCTATTGCATTATCATCTCC
AAGCTGTCACACTCCAAGGGCCACCAGAAGCGCAAGGCCCTCAAGACC
ACAGTCATCCTCATCCTGGCTTTCTTCGCCTGTTGGCTGCCTTACTAC
ATTGGGATCAGCATCGACTCCTTCATCCTCCTGGAAATCATCAAGCAA
GGGTGTGAGTTTGAGAACACTGTGCACAAGTGGATTTCCATCACCGAG
GCCCTAGCTTTCTTCCACTGTTGTCTGAACCCCATCCTCTATGCTTTC
CTTGGAGCCAAATTTAAAACCTCTGCCCAGCACGCACTCACCTCTGTG
AGCAGAGGGTCCAGCCTCAAGATCCTCTCCAAAGGAAAGCGAGGTGGA
CATTCATCTGTTTCCACTGAGTCTGAGTCTTCAAGTTTTCACTCCAGC
TAA
```

In one embodiment, the amino acid sequence of CXCR4 is:

(SEQ ID NO: 12)

```
MSIPLPLLQIYTSDNYTEEMGSGDYDSMKEPCFREENANFNKIFLPTI
```

-continued

```
YSIIFLTGIVGNGLVILVMGYQKKLRSMTDKYRLHLSVADLLFVITLP
FWAVDAVANWYFGNFLCKAVHVIYTVNLYSSVLILAFISLDRYLAIVH
ATNSQRPRKLLAEKVVYVGVWIPALLLTIPDFIFANVSEADDRYICDR
FYPNDLWVVVFQFQHIMVGLILPGIVILSCYCIIISKLSHSKGHQKRK
ALKTTVILILAFFACWLPYYIGISIDSFILLEIIKQGCEFENTVHKWI
SITEALAFFHCCLNPILYAFLGAKFKTSAQHALTSVSRGSSLKILSKG
KRGGHSSVSTESESSSFHSS
```

In one embodiment, the amino acid sequence of CXCR4 is:

(SEQ ID NO: 7)

```
MEGISIYTSDNYTEEMGSGDYDSMKEPCFREENANFNKIFLPTIYSII
FLTGIVGNGLVILVMGYQKKLRSMTDKYRLHLSVADLLFVITLPFWAV
DAVANWYFGNFLCKAVHVIYTVNLYSSVLILAFISLDRYLAIVHATNS
QRPRKLLAEKVVYVGVWIPALLLTIPDFIFANVSEADDRYICDRFYPN
DLWVVVFQFQHIMVGLILPGIVILSCYCIIISKLSHSKGHQKRKALKT
TVILILAFFACWLPYYIGISIDSFILLEIIKQGCEFENTVHKWISITE
ALAFFHCCLNPILYAFLGAKFKTSAQHALTSVSRGSSLKILSKGKRGG
HSSVSTESESSSFHSS
```

In one embodiment, the CXCR4 is encoded by a nucleotide sequence that has at least 70%, 80%, 90%, 95%, 96%, 97%, 98% 99% or 100% identity to SEQ ID NO: 9 or 6 (preferably SEQ ID NO: 9), preferably wherein the protein encoded by the nucleotide sequence substantially retains the natural function of the protein represented by SEQ ID NO: 7.

In one embodiment, the CXCR4 is encoded by a nucleotide sequence that encodes an amino acid sequence that has at least 70%, 80%, 90%, 95%, 96%, 97%, 98% 99% or 100% identity to SEQ ID NO: 7, preferably wherein the amino acid sequence substantially retains the natural function of the protein represented by SEQ ID NO: 7.

In one embodiment, the CXCR4 comprises or consists of an amino acid sequence that has at least 70%, 80%, 90%, 95%, 96%, 97%, 98% 99% or 100% identity to SEQ ID NO: 7, preferably wherein the amino acid sequence substantially retains the natural function of the protein represented by SEQ ID NO: 7.

In one embodiment, the CXCR4 is encoded by a nucleotide sequence that has at least 70%, 80%, 90%, 95%, 96%, 97%, 98% 99% or 100% identity to SEQ ID NO: 6, 9, 10 or 11, preferably wherein the protein encoded by the nucleotide sequence substantially retains the natural function of the protein represented by SEQ ID NO: 7 or 12.

In one embodiment, the CXCR4 is encoded by a nucleotide sequence that encodes an amino acid sequence that has at least 70%, 80%, 90%, 95%, 96%, 97%, 98% 99% or 100% identity to SEQ ID NO: 7 or 12, preferably wherein the amino acid sequence substantially retains the natural function of the protein represented by SEQ ID NO: 7 or 12.

In one embodiment, the CXCR4 comprises or consists of an amino acid sequence that has at least 70%, 80%, 90%, 95%, 96%, 97%, 98% 99% or 100% identity to SEQ ID NO: 7 or 12, preferably wherein the amino acid sequence substantially retains the natural function of the protein represented by SEQ ID NO: 7 or 12.

In one embodiment, the CXCR4 is a truncated CXCR4. In one embodiment, the CXCR4 is a CXCR4 Whim isoform (Kawai T. et al. (2005) Experimental Hematology; the CXCR4 Whim isoform I may be naturally expressed in subjects with Whim syndrome).

In one embodiment, the CXCR4 is a CXCR4 Whim isoform I. In one embodiment, the CXCR4 is a CXCR4 Whim isoform II.

An example nucleotide sequence encoding CXCR4 Whim isoform I is:

(SEQ ID NO: 13)

```
ATGTCCATTCCTTTGCCTCTTTTGCAGATATACACTTCAGATAACTAC
ACCGAGGAAATGGGCTCAGGGGACTATGACTCCATGAAGGAACCCTGT
TTCCGTGAAGAAAATGCTAATTTCAATAAAATCTTCCTGCCCACCATC
TACTCCATCATCTTCTTAACTGGCATTGTGGGCAATGGATTGGTCATC
CTGGTCATGGGTTACCAGAAGAAACTGAGAAGCATGACGGACAAGTAC
AGGCTGCACCTGTCAGTGGCCGACCTCCTCTTTGTCATCACGCTTCCC
TTCTGGGCAGTTGATGCCGTGGCAAACTGGTACTTTGGGAACTTCCTA
TGCAAGGCAGTCCATGTCATCTACACAGTCAACCTCTACAGCAGTGTC
CTCATCCTGGCCTTCATCAGTCTGGACCGCTACCTGGCCATCGTCCAC
GCCACCAACAGTCAGAGGCCAAGGAAGCTGTTGGCTGAAAAGGTGGTC
TATGTTGGCGTCTGGATCCCTGCCCTCCTGCTGACTATTCCCGACTTC
ATCTTTGCCAACGTCAGTGAGGCAGATGACAGATATATCTGTGACCGC
TTCTACCCCAATGACTTGTGGGTGGTTGTGTTCCAGTTTCAGCACATC
ATGGTTGGCCTTATCCTGCCTGGTATTGTCATCCTGTCCTGCTATTGC
ATTATCATCTCCAAGCTGTCACACTCCAAGGGCCACCAGAAGCGCAAG
GCCCTCAAGACCACAGTCATCCTCATCCTGGCTTTCTTCGCCTGTTGG
CTGCCTTACTACATTGGGATCAGCATCGACTCCTTCATCCTCCTGGAA
ATCATCAAGCAAGGGTGTGAGTTTGAGAACACTGTGCACAAGTGGATT
TCCATCACCGAGGCCCTAGCTTTCTTCCACTGTTGTCTGAACCCCATC
CTCTATGCTTTCCTTGGAGCCAAATTTAAAACCTCTGCCCAGCACGCA
CTCACCTCTGTGAGCAGAGGGTCCAGCCTCAAGATCCTCTCCAAAGGA
AAGTGAGGTGGACATTCATCTGTTTCCACTGAGTCTGAGTCTTCAAGT
TTTCACTCCAGCTAA
```

Another example nucleotide sequence encoding CXCR4 Whim isoform I is:

(SEQ ID NO: 14)

```
ATGTCTATTCCTCTGCCCCTGCTGCAGATCTACACCAGCGACAACTAC
ACCGAGGAAATGGGCAGCGGCGACTACGACAGCATGAAGGAACCCTGC
TTCCGGGAAGAGAACGCCAACTTCAACAAGATCTTCCTGCCCACAATC
TACAGCATCATCTTTCTGACCGGCATCGTGGGCAACGGACTCGTGATC
CTCGTGATGGGCTACCAGAAAAAGCTGCGGAGCATGACCGACAAGTAC
CGGCTGCACCTGAGCGTGGCCGACCTGCTGTTCGTGATCACCCTGCCT
```

-continued

```
TTCTGGGCCGTGGACGCCGTGGCCAATTGGTACTTCGGCAACTTCCTG
TGCAAGGCCGTGCACGTGATCTACACAGTGAACCTGTACAGCAGCGTG
CTGATCCTGGCCTTCATCAGCCTGGACAGATACCTGGCCATCGTGCAC
GCCACCAACAGCCAGCGGCCTAGAAAGCTGCTGGCCGAGAAGGTGGTG
TACGTGGGCGTGTGGATTCCCGCCCTGCTGCTGACCATCCCCGACTTC
ATCTTCGCCAACGTGTCCGAGGCCGACGACCGGTACATCTGCGACCGG
TTCTACCCCAACGACCTGTGGGTGGTGGTGTTCCAGTTCCAGCACATC
ATGGTGGGACTGATCCTGCCTGGCATCGTGATTCTGAGCTGCTACTGC
ATCATCATCAGCAAGCTGAGCCACAGCAAGGGCCACCAGAAGCGGAAG
GCCCTGAAAACCACCGTGATCCTGATTCTGGCTTTCTTCGCCTGCTGG
CTGCCCTACTACATCGGCATCAGCATCGACAGCTTCATCCTGCTGGAA
ATCATCAAGCAGGGCTGCGAGTTCGAGAACACCGTGCACAAGTGGATC
AGCATTACCGAGGCCCTGGCCTTTTTCCACTGCTGCCTGAACCCTATC
CTGTACGCCTTCCTGGGCGCCAAGTTCAAGACCTCTGCCCAGCACGCC
CTGACCAGCGTGTCCAGAGGAAGCAGCCTGAAGATCCTGAGCAAGGGC
AAGTGAGGCGGCCACAGCTCCGTGTCTACAGAGAGCGAGAGCAGCAGC
TTCCACAGCAGCTGA
```

An example amino acid sequence of CXCR4 Whim isoform I is:

(SEQ ID NO: 15)

```
MSIPLPLLQIYTSDNYTEEMGSGDYDSMKEPCFREENANFNKIFLPTI
YSIIFLTGIVGNGLVILVMGYQKKLRSMTDKYRLHLSVADLLFVITLP
FWAVDAVANWYFGNFLCKAVHVIYTVNLYSSVLILAFISLDRYLAIVH
ATNSQRPRKLLAEKVVYVGVWIPALLLTIPDFIFANVSEADDRYICDR
FYPNDLWVVVFQFQHIMVGLILPGIVILSCYCIIISKLSHSKGHQKRK
ALKTTVILILAFFACWLPYYIGISIDSFILLEIIKQGCEFENTVHKWI
SITEALAFFHCCLNPILYAFLGAKFKTSAQHALTSVSRGSSLKILSKG
K
```

An example nucleotide sequence encoding CXCR4 Whim isoform II is:

(SEQ ID NO: 16)

```
ATGGAGGGGATCAGTATATACACTTCAGATAACTACACCGAGGAAATG
GGCTCAGGGGACTATGACTCCATGAAGGAACCCTGTTTCCGTGAAGAA
AATGCTAATTTCAATAAAATCTTCCTGCCCACCATCTACTCCATCATC
TTCTTAACTGGCATTGTGGGCAATGGATTGGTCATCCTGGTCATGGGT
TACCAGAAGAAACTGAGAAGCATGACGGACAAGTACAGGCTGCACCTG
TCAGTGGCCGACCTCCTCTTTGTCATCACGCTTCCCTTCTGGGCAGTT
GATGCCGTGGCAAACTGGTACTTTGGGAACTTCCTATGCAAGGCAGTC
CATGTCATCTACACAGTCAACCTCTACAGCAGTGTCCTCATCCTGGCC
TTCATCAGTCTGGACCGCTACCTGGCCATCGTCCACGCCACCAACAGT
CAGAGGCCAAGGAAGCTGTTGGCTGAAAAGGTGGTCTATGTTGGCGTC
```

-continued

```
TGGATCCCTGCCCTCCTGCTGACTATTCCCGACTTCATCTTTGCCAAC
GTCAGTGAGGCAGATGACAGATATATCTGTGACCGCTTCTACCCCAAT
GACTTGTGGGTGGTTGTGTTCCAGTTTCAGCACATCATGGTTGGCCTT
ATCCTGCCTGGTATTGTCATCCTGTCCTGCTATTGCATTATCATCTCC
AAGCTGTCACACTCCAAGGGCCACCAGAAGCGCAAGGCCCTCAAGACC
ACAGTCATCCTCATCCTGGCTTTCTTCGCCTGTTGGCTGCCTTACTAC
ATTGGGATCAGCATCGACTCCTTCATCCTCCTGGAAATCATCAAGCAA
GGGTGTGAGTTTGAGAACACTGTGCACAAGTGGATTTCCATCACCGAG
GCCCTAGCTTTCTTCCACTGTTGTCTGAACCCCATCCTCTATGCTTTC
CTTGGAGCCAAATTTAAAACCTCTGCCCAGCACGCACTCACCTCTGTG
AGCAGAGGGTCCAGCCTCAAGATCCTCTCCAAAGGAAAGTGAGGTGGA
CATTCATCTGTTTCCACTGAGTCTGAGTCTTCAAGTTTTCACTCCAGC
TAA
```

Another example nucleotide sequence encoding CXCR4 Whim isoform II is:

(SEQ ID NO: 17)

```
ATGGAAGGCATCAGCATCTACACCAGCGACAACTACACCGAGGAAATG
GGCAGCGGCGACTACGACAGCATGAAGGAACCCTGCTTCCGGGAAGAG
AACGCCAACTTCAACAAGATCTTCCTGCCCACAATCTACAGCATCATC
TTTCTGACCGGCATCGTGGGCAACGGACTCGTGATCCTCGTGATGGGC
TACCAGAAAAAGCTGCGGAGCATGACCGACAAGTACCGGCTGCACCTG
AGCGTGGCCGACCTGCTGTTCGTGATCACCCTGCCTTTCTGGGCCGTG
GACGCCGTGGCCAATTGGTACTTCGGCAACTTCCTGTGCAAGGCCGTG
CACGTGATCTACACAGTGAACCTGTACAGCAGCGTGCTGATCCTGGCC
TTCATCAGCCTGGACAGATACCTGGCCATCGTGCACGCCACCAACAGC
CAGCGGCCTAGAAAGCTGCTGGCCGAGAAGGTGGTGTACGTGGGCGTG
TGGATTCCCGCCCTGCTGCTGACCATCCCCGACTTCATCTTCGCCAAC
GTGTCCGAGGCCGACGACCGGTACATCTGCGACCGGTTCTACCCCAAC
GACCTGTGGGTGGTGGTGTTCCAGTTCCAGCACATCATGGTGGGACTG
ATCCTGCCTGGCATCGTGATTCTGAGCTGCTACTGCATCATCATCAGC
AAGCTGAGCCACAGCAAGGGCCACCAGAAGCGGAAGGCCCTGAAAACC
ACCGTGATCCTGATTCTGGCTTTCTTCGCCTGCTGGCTGCCCTACTAC
ATCGGCATCAGCATCGACAGCTTCATCCTGCTGGAAATCATCAAGCAG
GGCTGCGAGTTCGAGAACACCGTGCACAAGTGGATCAGCATTACCGAG
GCCCTGGCCTTTTTCCACTGCTGCCTGAACCCTATCCTGTACGCCTTC
CTGGGCGCCAAGTTCAAGACCTCTGCCCAGCACGCCCTGACCAGCGTG
TCCAGAGGAAGCAGCCTGAAGATCCTGAGCAAGGGCAAGTGAGGCGGC
CACAGCTCCGTGTCTACAGAGAGCGAGAGCAGCAGCTTCCACAGCAGC
TGA
```

An example amino acid sequence of CXCR4 Whim isoform II is:

(SEQ ID NO: 18)

```
MEGISIYTSDNYTEEMGSGDYDSMKEPCFREENANFNKIFLPTIYSII
FLTGIVGNGLVILVMGYQKKLRSMTDKYRLHLSVADLLFVITLPFWAV
DAVANWYFGNFLCKAVHVIYTVNLYSSVLILAFISLDRYLAIVHATNS
QRPRKLLAEKVVYVGVWIPALLLTIPDFIFANVSEADDRYICDRFYPN
DLWVVVFQFQHIMVGLILPGIVILSCYCIIISKLSHSKGHQKRKALKT
TVILILAFFACWLPYYIGISIDSFILLEIIKQGCEFENTVHKWISITE
ALAFFHCCLNPILYAFLGAKFKTSAQHALTSVSRGSSLKILSKGK
```

In one embodiment, the CXCR4 is encoded by a nucleotide sequence that has at least 70%, 80%, 90%, 95%, 96%, 97%, 98% 99% or 100% identity to SEQ ID NO: 13, 14, 16 or 17, preferably wherein the protein encoded by the nucleotide sequence substantially retains the natural function of the protein represented by SEQ ID NO: 15 or 18.

In one embodiment, the CXCR4 is encoded by a nucleotide sequence that encodes an amino acid sequence that has at least 70%, 80%, 90%, 95%, 96%, 97%, 98% 99% or 100% identity to SEQ ID NO: 15 or 18, preferably wherein the amino acid sequence substantially retains the natural function of the protein represented by SEQ ID NO: 15 or 18.

In one embodiment, the CXCR4 comprises or consists of an amino acid sequence that has at least 70%, 80%, 90%, 95%, 96%, 97%, 98% 99% or 100% identity to SEQ ID NO: 15 or 18, preferably wherein the amino acid sequence substantially retains the natural function of the protein represented by SEQ ID NO: 15 or 18.

In a preferred embodiment, the CXCR4 is encoded by a nucleotide sequence that has at least 70%, 80%, 90%, 95%, 96%, 97%, 98% 99% or 100% identity to SEQ ID NO: 14, preferably wherein the protein encoded by the nucleotide sequence substantially retains the natural function of the protein represented by SEQ ID NO: 15.

Cell Survival and Engraftment

The term "survival" as used herein refers to the ability of the haematopoietic stem and/or progenitor cells to remain alive (e.g. not die or become apoptotic) during in vitro or ex vivo culture. Haematopoietic stem and/or progenitor cells may undergo, for example, increased apoptosis following transduction with a vector during cell culture; thus, the surviving cells may have avoided apoptosis and/or cell death.

Cell survival may be readily analysed by the skilled person. For example, the numbers of live, dead and/or apoptotic cells in a cell culture may be quantified at the beginning of culture and/or following culture for a period of time (e.g. about 6 or 12 hours, or 1, 2, 3, 4, 5, 6, 7 or more days; preferably, the period of time begins with the transduction of the cells with a vector). The effect of an agent on cell survival may be assessed by comparing the numbers and/or percentages of live, dead and/or apoptotic cells at the beginning and/or end of the culture period between experiments carried out in the presence and absence of the agent, but under otherwise substantially identical conditions.

Cell numbers and/or percentages in certain states (e.g. live, dead or apoptotic cells) may be quantified using any of a number of methods known in the art, including use of haemocytometers, automated cell counters, flow cytometers and fluorescence activated cell sorting machines. These techniques may enable distinguishing between live, dead and/or apoptotic cells. In addition or in the alternative, apoptotic cells may be detected using readily available apoptosis assays (e.g. assays based on the detection of phosphatidylserine (PS) on the cell membrane surface, such as through use of Annexin V, which binds to exposed PS; apoptotic cells may be quantified through use of fluorescently-labelled Annexin V), which may be used to complement other techniques.

The term "engraftment" as used herein refers to the ability of the haematopoietic stem and/or progenitor cells to populate and survive in a subject following their transplantation, i.e. in the short and/or long term after transplantation. For example, engraftment may refer to the number and/or percentages of haematopoietic cells descended from the transplanted haematopoietic stem and/or progenitor cells (e.g. graft-derived cells) that are detected about 1 day to 24 weeks, 1 day to 10 weeks, or 1-30 days or 10-30 days after transplantation. In the xenograft model of human haematopoietic stem and/or progenitor cell engraftment and repopulation, engraftment may be evaluated in the peripheral blood as the percentage of cells deriving from the human xenograft (e.g. positive for the CD45 surface marker), for example. In one embodiment, engraftment is assessed at about 1, 2, 3, 4, 5, 6, 7, 8, 9, 10, 15, 20, 25 or 30 days after transplantation. In another embodiment, engraftment is assessed at about 4, 5, 6, 7, 8, 9, 10, 11, 12, 13, 14, 15, 16, 17, 18, 19, 20, 21, 22, 23 or 24 weeks after transplantation. In another embodiment, engraftment is assessed at about 16-24 weeks, preferably 20 weeks, after transplantation.

Engraftment may be readily analysed by the skilled person. For example, the transplanted haematopoietic stem and/or progenitor cells may be engineered to comprise a marker (e.g. a reporter protein, such as a fluorescent protein), which can be used to quantify the graft-derived cells. Samples for analysis may be extracted from relevant tissues and analysed ex vivo (e.g. using flow cytometry).

Haematopoietic Stem and Progenitor Cells

A stem cell is able to differentiate into many cell types. A cell that is able to differentiate into all cell types is known as totipotent. In mammals, only the zygote and early embryonic cells are totipotent. Stem cells are found in most, if not all, multicellular organisms. They are characterised by the ability to renew themselves through mitotic cell division and differentiate into a diverse range of specialised cell types. The two broad types of mammalian stem cells are embryonic stem cells that are isolated from the inner cell mass of blastocysts, and adult stem cells that are found in adult tissues. In a developing embryo, stem cells can differentiate into all of the specialised embryonic tissues. In adult organisms, stem cells and progenitor cells act as a repair system for the body, replenishing specialised cells, but also maintaining the normal turnover of regenerative organs, such as blood, skin or intestinal tissues.

Haematopoietic stem cells (HSCs) are multipotent stem cells that may be found, for example, in peripheral blood, bone marrow and umbilical cord blood. HSCs are capable of self-renewal and differentiation into any blood cell lineage. They are capable of recolonising the entire immune system, and the erythroid and myeloid lineages in all the haematopoietic tissues (such as bone marrow, spleen and thymus). They provide for life-long production of all lineages of haematopoietic cells.

Haematopoietic progenitor cells have the capacity to differentiate into a specific type of cell. In contrast to stem cells however, they are already far more specific: they are pushed to differentiate into their "target" cell. A difference between stem cells and progenitor cells is that stem cells can replicate indefinitely, whereas progenitor cells can only divide a limited number of times. Haematopoietic progenitor cells can be rigorously distinguished from HSCs only by functional in vivo assay (i.e. transplantation and demonstration of whether they can give rise to all blood lineages over prolonged time periods).

The haematopoietic stem and progenitor cells of the invention comprise the CD34 cell surface marker (denoted as CD34+).

Haematopoietic Stem and/or Progenitor Cell (HSPC) Sources

A population of haematopoietic stem and/or progenitor cells (HSPCs) may be obtained from a tissue sample.

For example, a population of haematopoietic stem and/or progenitor cells may be obtained from peripheral blood (e.g. adult and foetal peripheral blood), umbilical cord blood, bone marrow, liver or spleen. Preferably, these cells are obtained from peripheral blood or bone marrow. They may be obtained after mobilisation of the cells in vivo by means of growth factor treatment.

In a preferred embodiment, the haematopoietic stem and/or progenitor cells are mobilised peripheral blood (mPB) haematopoietic stem and/or progenitor cells.

Mobilisation may be carried out using, for example, GCSF, Plerixafor, BIO5192, GROβ (GROβΔ4/CXCL2Δ4) (Fukuda, et al. (2007) Blood 110: 860-869) or combinations thereof. Other agents, such as NSAIDs and dipeptidyl peptidase inhibitors, may also be useful as mobilising agents.

With the availability of the stem cell growth factors GMCSF and GCSF, most haematopoietic stem cell transplantation procedures are now performed using stem cells collected from the peripheral blood, rather than from the bone marrow. Collecting peripheral blood stem cells provides a bigger graft, does not require that the donor be subjected to general anaesthesia to collect the graft, results in a shorter time to engraftment and may provide for a lower long-term relapse rate.

Bone marrow may be collected by standard aspiration methods (either steady-state or after mobilisation), or by using next-generation harvesting tools (e.g. Marrow Miner).

In addition, HSPCs may also be derived from induced pluripotent stem cells.

HSC Characteristics

HSCs are typically of low forward scatter and side scatter profile by flow cytometric procedures. Some are metabolically quiescent, as demonstrated by Rhodamine labelling which allows determination of mitochondrial activity. HSCs may comprise certain cell surface markers such as CD34, CD45, CD133, CD90 and CD49f. They may also be defined as cells lacking the expression of the CD38 and CD45RA cell surface markers. However, expression of some of these markers is dependent upon the developmental stage and tissue-specific context of the HSC. Some HSCs called "side population cells" exclude the Hoechst 33342 dye as detected by flow cytometry. Thus, HSCs have descriptive characteristics that allow for their identification and isolation.

Negative Markers

CD38 is the most established and useful single negative marker for human HSCs.

Human HSCs may also be negative for lineage markers such as CD2, CD3, CD14, CD16, CD19, CD20, CD24, CD36, CD56, CD66b, CD271 and CD45RA. However, these markers may need to be used in combination for HSC enrichment.

By "negative marker" it is to be understood that human HSCs lack the expression of these markers.

Positive Markers

CD34 and CD133 are the most useful positive markers for HSCs.

Some HSCs are also positive for lineage markers such as CD90, CD49f and CD93. However, these markers may need to be used in combination for HSC enrichment.

By "positive marker" it is to be understood that human HSCs express these markers.

In one embodiments, the HSPCs are CD34+. In a preferred embodiment, the HSPCs are CD34+CD38−.

Differentiated Cells

A differentiated cell is a cell which has become more specialised in comparison to a stem cell or progenitor cell. Differentiation occurs during the development of a multicellular organism as the organism changes from a single zygote to a complex system of tissues and cell types. Differentiation is also a common process in adults: adult stem cells divide and create fully-differentiated daughter cells during tissue repair and normal cell turnover. Differentiation dramatically changes a cell's size, shape, membrane potential, metabolic activity and responsiveness to signals. These changes are largely due to highly-controlled modifications in gene expression. In other words, a differentiated cell is a cell which has specific structures and performs certain functions due to a developmental process which involves the activation and deactivation of specific genes. Here, a differentiated cell includes differentiated cells of the haematopoietic lineage such as monocytes, macrophages, neutrophils, basophils, eosinophils, erythrocytes, megakaryocytes/platelets, dendritic cells, T-cells, B-cells and NK-cells. For example, differentiated cells of the haematopoietic lineage can be distinguished from stem cells and progenitor cells by detection of cell surface molecules which are not expressed or are expressed to a lesser degree on undifferentiated cells. Examples of suitable human lineage markers include CD33, CD13, CD14, CD15 (myeloid), CD19, CD20, CD22, CD79a (B), CD36, CD71, CD235a (erythroid), CD2, CD3, CD4, CD8 (T) and CD56 (NK).

Isolation and Enrichment of Populations of Cells

Populations of genetically engineered haematopoietic stem and/or progenitor cells (HSPCs) are disclosed herein. Preferably, the population of HSPCs is an isolated population of HSPCs.

By "isolated population" of cells it is to be understood that the population of cells is not comprised within the body. An isolated population of cells may have been previously removed from a subject. An isolated population of cells may be cultured and manipulated ex vivo or in vitro using standard techniques known in the art. An isolated population of cells may later be reintroduced into a subject. Said subject may be the same subject from which the cells were originally isolated or a different subject.

A population of cells may be purified selectively for cells that exhibit a specific phenotype or characteristic, and from other cells which do not exhibit that phenotype or characteristic, or exhibit it to a lesser degree. For example, a population of cells that expresses a specific marker (such as CD34) may be purified from a starting population of cells. Alternatively, or in addition, a population of cells that does not express another marker (such as CD38) may be purified.

By "enriching" a population of cells for a certain type of cells it is to be understood that the concentration of that type of cells is increased within the population. The concentration of other types of cells may be concomitantly reduced.

Purification or enrichment may result in the population of cells being substantially pure of other types of cell.

Purifying or enriching for a population of cells expressing a specific marker (e.g. CD34 or CD38) may be achieved by using an agent that binds to that marker, preferably substantially specifically to that marker.

An agent that binds to a cellular marker may be an antibody, for example an anti-CD34 or anti-CD38 antibody.

The term "antibody" refers to complete antibodies or antibody fragments capable of binding to a selected target, and including Fv, ScFv, F(ab') and $F(ab')_2$, monoclonal and polyclonal antibodies, engineered antibodies including chimeric, CDR-grafted and humanised antibodies, and artificially selected antibodies produced using phage display or alternative techniques.

In addition, alternatives to classical antibodies may also be used in the invention, for example "avibodies", "avimers", "anticalins", "nanobodies" and "DARPins".

The agents that bind to specific markers may be labelled so as to be identifiable using any of a number of techniques known in the art. The agent may be inherently labelled, or may be modified by conjugating a label thereto. By "conjugating" it is to be understood that the agent and label are operably linked. This means that the agent and label are linked together in a manner which enables both to carry out their function (e.g. binding to a marker, allowing fluorescent identification, or allowing separation when placed in a magnetic field) substantially unhindered. Suitable methods of conjugation are well known in the art and would be readily identifiable by the skilled person.

A label may allow, for example, the labelled agent and any cell to which it is bound to be purified from its environment (e.g. the agent may be labelled with a magnetic bead or an affinity tag, such as avidin), detected or both. Detectable markers suitable for use as a label include fluorophores (e.g. green, cherry, cyan and orange fluorescent proteins) and peptide tags (e.g. His tags, Myc tags, FLAG tags and HA tags).

A number of techniques for separating a population of cells expressing a specific marker are known in the art. These include magnetic bead-based separation technologies (e.g. closed-circuit magnetic bead-based separation), flow cytometry, fluorescence-activated cell sorting (FACS), affinity tag purification (e.g. using affinity columns or beads, such as biotin columns to separate avidin-labelled agents) and microscopy-based techniques.

It may also be possible to perform the separation using a combination of different techniques, such as a magnetic bead-based separation step followed by sorting of the resulting population of cells for one or more additional (positive or negative) markers by flow cytometry.

Clinical grade separation may be performed, for example, using the CliniMACS® system (Miltenyi). This is an example of a closed-circuit magnetic bead-based separation technology.

It is also envisaged that dye exclusion properties (e.g. side population or rhodamine labelling) or enzymatic activity (e.g. ALDH activity) may be used to enrich for HSCs.

Gene Editing

The term "gene editing" refers to a type of genetic engineering in which a nucleic acid is inserted, deleted or replaced in a cell. Gene editing may be achieved using engineered nucleases, which may be targeted to a desired site in a polynucleotide (e.g. a genome). Such nucleases may create site-specific double-strand breaks at desired locations, which may then be repaired through non-homologous end-joining (NHEJ) or homologous recombination (HR), resulting in targeted mutations.

Such nucleases may be delivered to a target cell using vectors, such as viral vectors.

Examples of suitable nucleases known in the art include zinc finger nucleases (ZFNs), transcription activator like effector nucleases (TALENs), and the clustered regularly interspaced short palindromic repeats (CRISPR)/Cas system (Gaj, T. et al. (2013) Trends Biotechnol. 31: 397-405; Sander, J. D. et al. (2014) Nat. Biotechnol. 32: 347-55).

Meganucleases (Silve, G. et al. (2011) Cur. Gene Ther. 11: 11-27) may also be employed as suitable nucleases for gene editing.

The CRISPR/Cas system is an RNA-guided DNA binding system (van der Oost et al. (2014) Nat. Rev. Microbiol. 12: 479-92), wherein the guide RNA (gRNA) may be selected to enable a Cas9 domain to be targeted to a specific sequence. Methods for the design of gRNAs are known in the art. Furthermore, fully orthogonal Cas9 proteins, as well as Cas9/gRNA ribonucleoprotein complexes and modifications of the gRNA structure/composition to bind different proteins, have been recently developed to simultaneously and directionally target different effector domains to desired genomic sites of the cells (Esvelt et al. (2013) Nat. Methods 10: 1116-21; Zetsche, B. et al. (2015) Cell pii: S0092-8674 (15)01200-3; Dahlman, J. E. et al. (2015) Nat. Biotechnol. 2015 Oct. 5. doi: 10.1038/nbt.3390. [Epub ahead of print]; Zalatan, J. G. et al. (2015) Cell 160: 339-50; Paix, A. et al. (2015) Genetics 201: 47-54), and are suitable for use in the invention.

Vector

A vector is a tool that allows or facilitates the transfer of an entity from one environment to another. In accordance with the present invention, and by way of example, some vectors used in recombinant nucleic acid techniques allow entities, such as a segment of nucleic acid (e.g. a heterologous DNA segment, such as a heterologous cDNA segment), to be transferred into a target cell. The vector may serve the purpose of maintaining the heterologous nucleic acid (DNA or RNA) within the cell, facilitating the replication of the vector comprising a segment of nucleic acid, or facilitating the expression of the protein encoded by a segment of nucleic acid.

Vectors may be non-viral or viral. Examples of vectors used in recombinant nucleic acid techniques include, but are not limited to, plasmids, chromosomes, artificial chromosomes and viruses. The vector may be single stranded or double stranded. It may be linear and optionally the vector comprises one or more homology arms. The vector may also be, for example, a naked nucleic acid (e.g. DNA). In its simplest form, the vector may itself be a nucleotide of interest.

The vectors used in the invention may be, for example, plasmid or virus vectors and may include a promoter for the expression of a polynucleotide and optionally a regulator of the promoter.

Vectors comprising polynucleotides used in the invention may be introduced into cells using a variety of techniques known in the art, such as transformation, transfection and transduction. Several techniques are known in the art, for example transduction with recombinant viral vectors, such as retroviral, lentiviral, adenoviral, adeno-associated viral, baculoviral and herpes simplex viral vectors, Sleeping Beauty vectors; direct injection of nucleic acids and biolistic transformation.

Non-viral delivery systems include but are not limited to DNA transfection methods. Here, transfection includes a process using a non-viral vector to deliver a gene to a target cell. Typical transfection methods include electroporation, DNA biolistics, lipid-mediated transfection, compacted DNA-mediated transfection, liposomes, immunoliposomes, lipofectin, cationic agent-mediated transfection, cationic facial amphiphiles (CFAs) (Nature Biotechnology (1996) 14: 556) and combinations thereof.

The term "vector" includes an expression vector, i.e. a construct capable of in vivo or in vitro/ex vivo expression. Expression may be controlled by a vector sequence, or, for example in the case of insertion at a target site, expression may be controlled by a target sequence. A vector may be integrated or tethered to the cell's DNA.

Viral delivery systems include but are not limited to adenoviral vectors, adeno-associated viral (AAV) vectors, herpes viral vectors, retroviral vectors, lentiviral vectors and baculoviral vectors.

In one embodiment, the vector is a Sendai viral vector. Sendai viral vectors may be particularly effective for transient expression of transgenes, such as CD47 and/or CXCR4. Furthermore, Sendai viral vectors are typically capable of very efficiently transferring transgenes to HSPCs (e.g. capable of transferring a transgene (e.g. GFP) to cord blood CD34+ cells at an MOI of 3).

Sendai viral vectors are typically unable to infect neighbouring cells. In addition, Sendai viral vectors may be temperature sensitive, for example: at a temperature of about 34° C. they may be capable of replication; at a temperature of about 37° C. their replication may be low; and at a temperature of about 38° C. they replication may be prevented. Sendai viral vectors typically do not impact cell viability.

Nucleotide of Interest

In addition to CD47 and/or CXCR4, the HSPCs may be further genetically engineered to express a transgene. The transgene may be a nucleotide of interest (NOI).

Preferably the nucleotide of interest gives rise to a therapeutic effect.

Suitable NOIs include, but are not limited to, sequences encoding enzymes, cytokines, chemokines, hormones, antibodies, anti-oxidant molecules, engineered immunoglobulin-like molecules, single chain antibodies, fusion proteins, immune co-stimulatory molecules, immunomodulatory molecules, anti-sense RNA, microRNA, shRNA, siRNA, ribozymes, miRNA target sequences, a transdomain negative mutant of a target protein, toxins, conditional toxins, antigens, tumour suppressor proteins, growth factors, transcription factors, membrane proteins, surface receptors, anti-cancer molecules, vasoactive proteins and peptides, anti-viral proteins and ribozymes, and derivatives thereof (such as derivatives with an associated reporter group). The NOIs may also encode pro-drug activating enzymes.

An example of a NOI is the beta-globin chain which may be used for gene therapy of thalassemia/sickle cell disease.

NOIs also include those useful for the treatment of other diseases requiring non-urgent/elective gene correction in the myeloid lineage such as: chronic granulomatous disease (CGD, e.g. the gp91phox transgene), leukocyte adhesion defects, other phagocyte disorders in patients without ongoing severe infections and inherited bone marrow failure syndromes (e.g. Fanconi anaemia), as well as primary immunodeficiencies (SCIDs).

NOIs also include those useful in the treatment of lysosomal storage disorders and immunodeficiencies.

Pharmaceutical Composition

The cells of the invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of cell therapy products is preferably performed in compliance with FACT-JACIE International Standards for cellular therapy.

Haematopoietic Stem and/or Progenitor Cell Transplantation

The invention provides a population of haematopoietic stem and/or progenitor cells prepared according to a method of the invention for use in therapy, for example for use in gene therapy.

The use may be as part of a haematopoietic stem and/or progenitor cell transplantation procedure.

Haematopoietic stem cell transplantation (HSCT) is the transplantation of blood stem cells derived from the bone marrow (in this case known as bone marrow transplantation) or blood. Stem cell transplantation is a medical procedure in the fields of haematology and oncology, most often performed for people with diseases of the blood or bone marrow, or certain types of cancer.

Many recipients of HSCTs are multiple myeloma or leukaemia patients who would not benefit from prolonged treatment with, or are already resistant to, chemotherapy. Candidates for HSCTs include paediatric cases where the patient has an inborn defect such as severe combined immunodeficiency or congenital neutropenia with defective stem cells, and also children or adults with aplastic anaemia who have lost their stem cells after birth. Other conditions treated with stem cell transplants include sickle-cell disease, myelodysplastic syndrome, neuroblastoma, lymphoma, Ewing's Sarcoma, Desmoplastic small round cell tumour and Hodgkin's disease. More recently non-myeloablative, or so-called "mini transplant", procedures have been developed that require smaller doses of preparative chemotherapy and radiation. This has allowed HSCT to be conducted in the elderly and other patients who would otherwise be considered too weak to withstand a conventional treatment regimen.

In one embodiment, the population of haematopoietic stem and/or progenitor cells is administered as part of an autologous stem cell transplant procedure.

In another embodiment, the population of haematopoietic stem and/or progenitor cells is administered as part of an allogeneic stem cell transplant procedure.

By "autologous stem cell transplant procedure" it is to be understood that the starting population of cells (which may then be genetically engineered) is obtained from the same subject as that to which the engineered cell population is administered. Autologous transplant procedures are advantageous as they avoid problems associated with immunological incompatibility and are available to subjects irrespective of the availability of a genetically matched donor.

By "allogeneic stem cell transplant procedure" it is to be understood that the starting population of cells (which may then be genetically engineered) is obtained from a different subject as that to which the engineered cell population is administered. Preferably, the donor will be genetically matched to the subject to which the cells are administered to minimise the risk of immunological incompatibility.

In one embodiment, the subject is subjected to a mild myeloablative, reduced intensity or non-myeloablative conditioning regimen before administration of the HSPCs.

The inventors have found that the HSPCs of the invention are preferentially exchanged and/or selectively engrafted in subjects that have been subjected to mobilisation of their endogenous HSPCs. The transplanted HSPCs efficiently outcompete the endogenous HSPCs in repopulating the bone marrow In one embodiment, the subject is subjected to a regimen for mobilisation of endogenous HSPCs. Preferably, the regimen for mobilisation of endogenous HSPCs is administered before administration of the HSPCs of the invention.

In one embodiment, the subject is administered one or more HSPC mobilisation agents before administration of the HSPCs of the invention. In one embodiment, the subject is administered granulocyte colony stimulating factor (GCSF), Plerixafor and/or BIO5192 before administration of the HSPCs of the invention. In one embodiment, the subject is administered GROβ (GROβΔ4/CXCL2Δ4) and Plerixafor before administration of the HSPCs. Preferably, the HSPCs are genetically engineered to express CXCR4, or CD47 and CXCR4.

The invention may also utilise conditioning regimens that are based on the administration of toxins that targeted to HSPCs. Such methods may enable selective depletion or ablation of endogenous HSPC populations, and include those disclosed in US 2016/324982 for example. Such methods may be non-myeloablative. These methods may utilise one or more markers on the HSPC cell surface to target a toxin, such that the toxin is internalised by the HSPC. The methods may avoid toxicities associated with traditional conditioning methods.

In one embodiment, the subject subjected to conditioning with one or more HSPC-specific immunotoxins. Preferably, the one or more HSPC-specific immunotoxins are administered before administration of the HSPCs.

In one embodiment, the subject is administered an antibody conjugated to a toxin before administration of the HSPCs.

Suitable toxins include, but are not limited to saporin, diphtheria toxin, *pseudomonas* exotoxin A, Ricin A chain derivatives, a small molecule toxin, RNA polymerase II and/or III inhibitors (e.g. an amatoxin, such as α-amanitin, β-amanitin, γ-amanitin, ε-amanitin, amanin, amaninamide, amanullin or amanullinic acid), a DNA-damaging molecule (e.g. an anti-tubulin agent, a DNA crosslinking agent, a DNA alkylating agent or a mitotic disrupting agent; such as, maytansine) and combinations thereof.

Suitable antibodies include antibodies that bind to a cell surface protein selected from the group consisting of CD45, CD49d (VLA-4), CD49f (VLA-6), CD51, CD84, CD90, CD117, CD133, CD134 and CD184 (CXCR4).

In one embodiment, the immunotoxin is an anti-cKit immunotoxin. An anti-cKit immunotoxin may comprise an anti-cKit antibody conjugated to a toxin (see, for example, Czechowicz, A. et al. (2018) Biol Bone Marrow Transplant 24: S60 Abstract 54).

In one embodiment, the immunotoxin comprises an anti-cKit antibody. In one embodiment, the immunotoxin comprises a protein synthesis toxin, preferably a saporin. In a preferred embodiment, the immunotoxin is an anti-cKit-saporin immunotoxin.

In one embodiment, the immunotoxin comprises an anti-CD45 antibody. In one embodiment, the immunotoxin comprises a protein synthesis toxin, preferably a saporin. In a preferred embodiment, the immunotoxin is an anti-CD45-saporin immunotoxin.

Preferably, the HSPCs are administered to the subject after the toxin has dissipated from the bone marrow of the subject.

In one embodiment, the subject does not undergo chemotherapy or radiotherapy conditioning before administration of the HSPCs.

Suitable doses of transduced cell populations are such as to be therapeutically and/or prophylactically effective. The dose to be administered may depend on the subject and condition to be treated, and may be readily determined by a skilled person.

Haematopoietic progenitor cells provide short term engraftment. Accordingly, gene therapy by administering haematopoietic progenitor cells would provide a non-permanent effect in the subject. For example, the effect may be limited to 1-6 months following administration of the haematopoietic progenitor cells. An advantage of this approach would be better safety and tolerability, due to the self-limited nature of the therapeutic intervention.

Such haematopoietic progenitor cell gene therapy may be suited to treatment of acquired disorders, for example cancer, where time-limited expression of a (potentially toxic) anti-cancer nucleotide of interest may be sufficient to eradicate the disease.

The invention (e.g. the haematopoietic stem and/or progenitor cell gene therapy) may be, for example, useful in the treatment of a disease selected from the group consisting of mucopolysaccharidosis type I (MPS-1), chronic granulomatous disorder (CGD), Fanconi anaemia (FA), sickle cell disease, Pyruvate kinase deficiency (PKD), Leukocyte adhesion deficiency (LAD), metachromatic leukodystrophy (MLD), globoid cell leukodystrophy (GLD), $GM_2$ gangliosidosis, thalassemia, cancer, a genetic disease and a blood disease.

The invention may also be, for example, useful in the treatment of mucopolysaccharidoses disorders and other lysosomal storage disorders.

In addition, or in the alternative, the invention may be useful in the treatment of the disorders listed in WO 1998/005635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the invention may be useful in the treatment of the disorders listed in WO 1998/007859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); anti-inflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the invention may be useful in the treatment of the disorders listed in WO 1998/009985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Kit

In another aspect, the invention provides a kit comprising one or more vectors encoding CD47 and/or CXCR4, and/or cell populations of the invention.

The vectors and/or cell populations may be provided in suitable containers.

The kit may also include instructions for use.

Method of Treatment

It is to be appreciated that all references herein to treatment include curative, palliative and prophylactic treatment. The treatment of mammals, particularly humans, is preferred. Both human and veterinary treatments are within the scope of the invention.

Administration

Although the agents for use in the invention (in particular, the populations of cells) can be administered alone, they will generally be administered in admixture with a pharmaceutical carrier, excipient or diluent, particularly for human therapy.

Dosage

The skilled person can readily determine an appropriate dose of one of the agents of the invention to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy. There can of course be individual instances where higher or lower dosage ranges are merited, and such are within the scope of the invention.

Subject

A "subject" refers to either a human or non-human animal.

Examples of non-human animals include vertebrates, for example mammals, such as non-human primates (particularly higher primates), dogs, rodents (e.g. mice, rats or guinea pigs), pigs and cats. The non-human animal may be a companion animal.

Preferably, the subject is a human.

Variants, Derivatives, Analogues, Homologues and Fragments

In addition to the specific proteins and nucleotides mentioned herein, the invention also encompasses the use of variants, derivatives, analogues, homologues and fragments thereof.

In the context of the invention, a variant of any given sequence is a sequence in which the specific sequence of residues (whether amino acid or nucleic acid residues) has been modified in such a manner that the polypeptide or polynucleotide in question substantially retains its function. A variant sequence can be obtained by addition, deletion, substitution, modification, replacement and/or variation of at least one residue present in the naturally-occurring protein.

The term "derivative" as used herein, in relation to proteins or polypeptides of the invention includes any substitution of, variation of, modification of, replacement of, deletion of and/or addition of one (or more) amino acid residues from or to the sequence providing that the resultant protein or polypeptide substantially retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence substantially retains the required activity or ability. Amino acid substitutions may include the use of non-naturally occurring analogues.

Proteins used in the invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| | | |
|---|---|---|
| ALIPHATIC | Non-polar | G A P |
| | | I L V |
| | Polar-uncharged | C S T M |
| | | N Q |
| | Polar-charged | D E |
| | | K R H |
| AROMATIC | | F W Y |

The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 60%, 65%, 70%, 75%, 80%, 85%, 90%, 95% or 99% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the invention it is preferred to express homology in terms of sequence identity.

A homologous sequence may include a nucleotide sequence which may be at least 50%, 55%, 60%, 65%, 70%, 75%, 80%, 85% or 90% identical, preferably at least 95% or 97% or 99% identical to the subject sequence. Although homology can also be considered in terms of similarity, in the context of the invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Res. 12: 387). Examples of other software that can perform sequence comparisons include, but are not limited to, the BLAST package (see Ausubel et al. (1999) ibid—Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing protein and nucleotide sequences (see FEMS Microbiol. Lett. (1999) 174: 247-50; FEMS Microbiol. Lett. (1999) 177: 187-8).

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result.

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1

Methods

Cells

Cord blood CD34+ cells (Lonza, Stem Cell Technologies) were used for all experiments. Cells were maintained in Stem Span medium supplemented with cytokines (SCF, Flt3, IL6 and TPO).

Stable Overexpression

CD34+ cells were maintained overnight after thawing in Stem Span medium supplemented with cytokines (SCF, Flt3, IL6 and TPO). Cells were then transduced at MOI 100 with a bi-directional lentiviral vector co-expressing CXCR4 and GFP; CD47 and GFP; or NGFR and GFP as a control. After 14 h, cells were washed and transplanted into NSG mice.

Gene Editing and Transient Overexpression

CD34+ cells were maintained after thawing for 3 days for expansion in Stem Span medium supplemented with cytokines (SCF, Flt3, IL6, TPO, SR1 and UM171). Cells were electroporated with the protein Cas9 and RNPs directed against the AAVS1 locus and HPLC purified (CXCR4, CD47 or GFP as a control) RNA (Lonza protocol).

15 minutes after electroporation, AAV6-GFP donor vector was added to cells at MOI 5.104. 6 h after treatment, cells were engrafted into NSG mice.

Mice

NSG (NODSCIDIL2Ry$^{-/-}$; Charles River) were used for all in vivo experiments. Transplanted mice were irradiated (200 rad) 4 h before engraftment.

HSC Engraftment

Cells were engrafted into NSG mice via tail vein injection ($10^5$ cells/mouse).

HSC Mobilisation

Mice were surgically implanted with osmotic pumps delivering GCSF (250 μg/kg/day) for 7 days (alzet micro-osmotic pump model 1007D). At days 6 and 7, mice received intraperitoneally (IP) a single BIO5192 injection at 1 mg/kg and a single Plerixafor injection at 5 mg/kg. At the end of the mobilisation treatment, mice were engrafted with stable CXCR4-GFP overexpression or NGFR-GFP (control) CD34+ cells.

Engraftment Evaluation In Vivo

Every 4 weeks after engraftment, mice were bled to evaluate human cell engraftment percentage. Blood was recovered into EDTA and stained with FACS antibodies (hCD45, CD33, CD19, CD13, CD3 and CXCR4). Red blood cells were lysed and blood was washed with Macs buffer before FACS analysis (Canto, DIVA software).

Results

Potential targets were exploited for transiently endowing edited HSCs with engraftment and/or growth advantage in vivo. We overexpressed genes with established functions in HSCs, such as CD47 and CXCR4 expressed at the HSC membrane and involved in phagocytosis protection and homing, respectively.

First, we measured biological advantages of CD47 and/or CXCR4 stable overexpression (OE) by scoring overall engraftment of the treated cells in NSG competitive transplantation. Preliminary results obtained with HSPC that stably overexpress CXCR4-GFP or CD47-GFP show significantly increased early or long-term engraftment, respectively, with a promising increase compared to control (FIG. 1).

Figure 2:
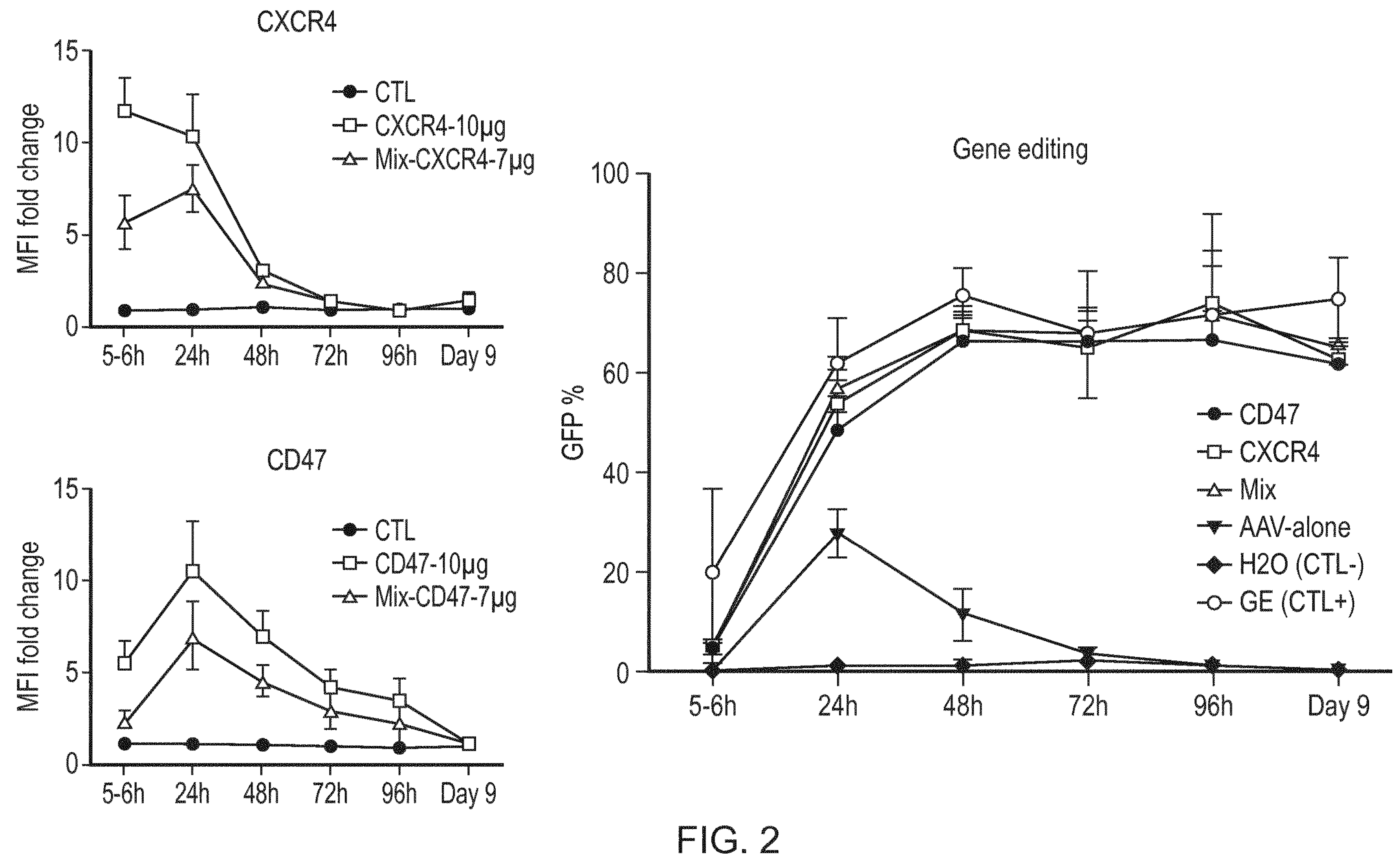

Stable overexpression of CD47 and CXCR4 gives engraftment advantage in vivo. However, future clinical applications will require transient overexpression of these two targets. We thus validated the transient overexpression of our targets alone or in combination coupled to gene editing (GE) by co-electroporation with nucleases. Effect in vitro was evaluated (FIG. 2).

In vitro, we were able to transiently overexpress our targets without impacting gene editing efficiency.

Figure 3:
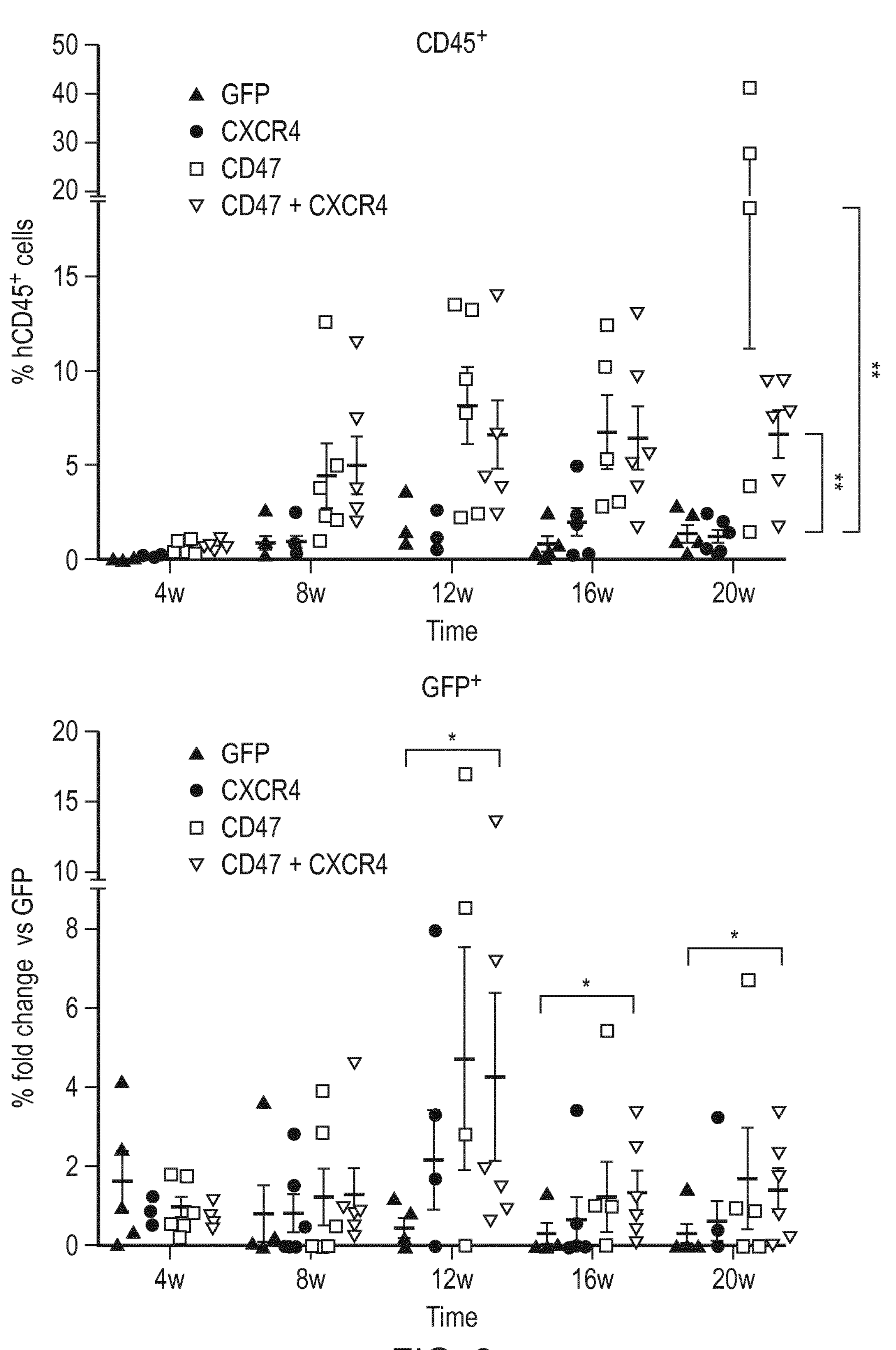

Transient overexpression of our targets, alone or in combination was evaluated in vivo by following engraftment and outgrowth of the gene edited (GFP gene inserted into the AAVS1 locus) HSPCs (FIG. 3).

Transient overexpression of CD47 alone or in combination with CXCR4 showed an improved engraftment of gene edited cells.

These targets were then used to favour exchange and/or selective engraftment and expansion of the gene-edited HSCs during treatment inducing mobilisation of endogenous HSCs.

We first established an experimental model to study human HSC mobilisation from the bone marrow (BM) niche in NSG mice based on drugs currently used in clinic (GCSF, Plerixafor) (Dominges et al. (2016) Int J Hematol; Welschinger, R. et al. (2013) Exp Hematol 41: 293-302.e1).

Figure 4:
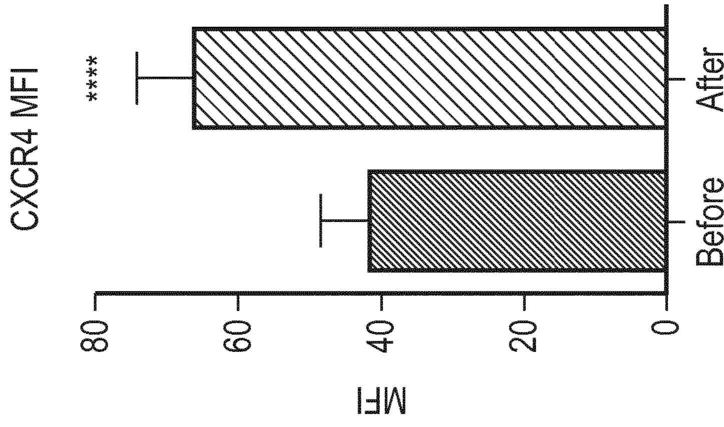
Figure 4:
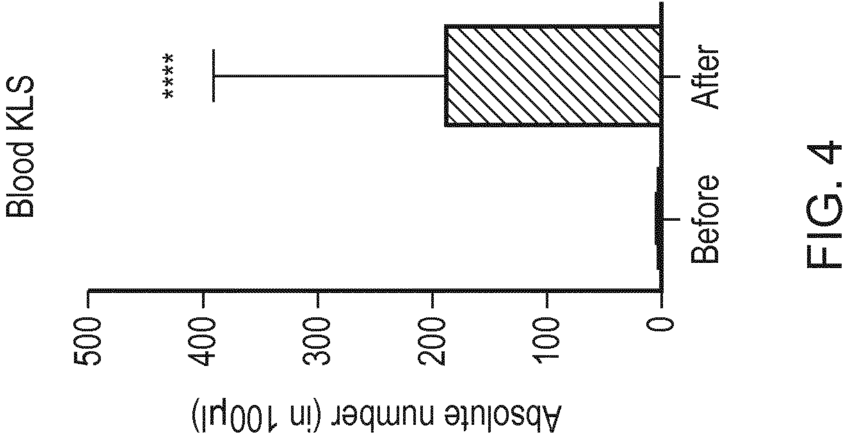
Figure 4:
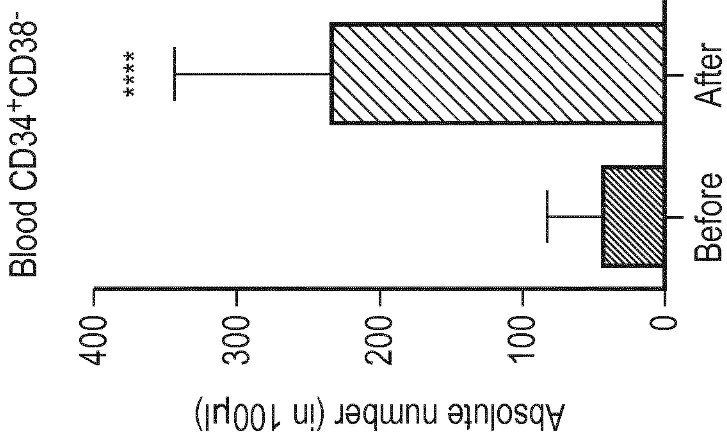

Briefly, NSG mice were first engrafted with CD34+ cells in order to pre-establish a human haematochimeric graft. Mice were then treated with the conditioning agents for mobilisation (see Methods, HSC Mobilisation). We validated in vivo our HSPC mobilisation protocol, with a significantly increase in number of circulating progenitor human cells (CD34+CD38−) and murine stem cells (Kit+; Lin−, Sca1+, KLS) (FIG. 4).

Figure 5:
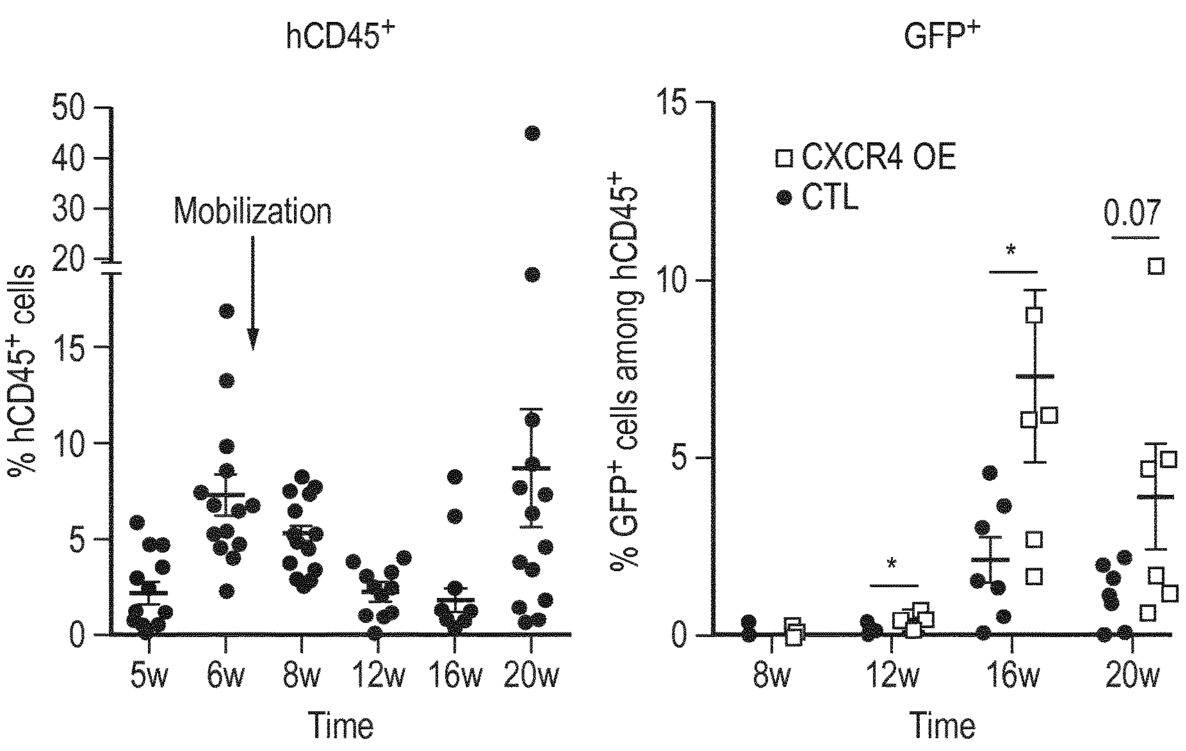
Figure 5:
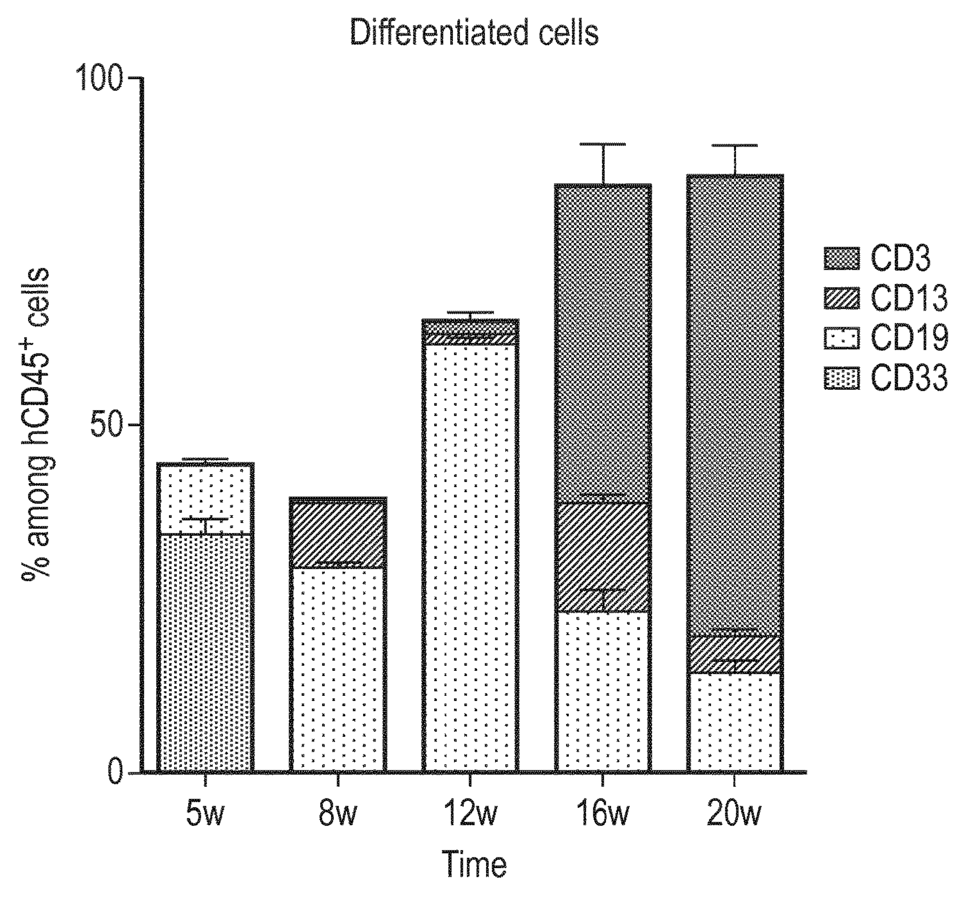

As our mobilisation protocol includes the injection of Plerixafor (also known as AMD3100), a specific antagonist of CXCR4 receptor, we decided to match CXCR4 overexpression advantage to Plerixafor mobilisation. Thus, we evaluated human HSPC mobilisation from the bone marrow niche followed by infusion of enhanced HSC (CXCR4 stable overexpression) from the same/matching donors as the original graft. NSG mice stably engrafted with human HSPC were treated for mobilisation (GCSF 250 μg/kg/day for 7 days with osmotic pumps; Plerixafor 5 mg/kg/day and BIO5192 1 mg/kg/day the last two days by IP injections [BIO5192, Ramirez, et al. (2009) Blood 114: 1340-1343]) then infused with gene marked control or CXCR4-GFP overexpressing cells from the same donor as the original transplant (FIG. 5).

Remarkably, CXCR4 overexpressing cells efficiently outcompeted the mobilised HSPCs and established stable chimerism at ≥7-9% in the human cell graft, while control cells were only detectable at 1-2% level.

Example 2

A strategy to improve the safety of conditioning is the use of antibodies that specifically target haematopoietic stem cells and other haematopoietic cells. Such conditioning regimens can minimise off-target toxicity and immunosuppression while enabling efficient engraftment (Palchaudhuri, R. et al. (2016) Nat Biotechnol 34: 738-745).

The engineered HSPCs disclosed herein will be studied in combination with conditioning regimens based on depletion using an immunotoxin, such as an anti-cKit immunotoxin.

The CD47 and/or CXCR4 are intended to favour exchange and/or selective engraftment and expansion of HSPCS, in particular gene-edited HSPCs during treatment inducing depletion of endogenous haematopoietic stem cells by specific antibodies.

Example 3

Methods

Cells

Cord blood CD34+ cells (Lonza, Stem Cell Technologies) were used for in vitro experiments. Cells were maintained in Stem Span medium supplemented with cytokines (SCF, Flt3, IL6 and TPO).

Mobilised Peripheral Blood (mPB) CD34+ cells were used for in vivo experiments. Cells were maintained in Stem Span medium supplemented with cytokines (SCF, Flt3, TPO, UM171, SR1).

Transient Overexpression

Cells were electroporated with HPLC purified (CXCR4, CD47 or GFP as a control) RNA (Lonza protocol). CXCR4, CD47 and CXCR4 expression levels were evaluated by staining with FACS antibodies (CXCR4, CD47) starting 6 hours after electroporation, for 4 days.

Mice

NSG (NODSCIDIL2Ry−/−; Charles River) were used for some in vivo experiments. Transplanted mice were irradiated (200 rad) 4 h before engraftment.

NSGW41 mice (NSG KitW41/W41; Charles River) were used for mobilisation experiments in vivo. These mice do not required irradiation prior the engraftment of human hematopoietic stem cells.

HSC Engraftment

Cells were engrafted into NSG or NSGW41 mice via tail vein injection ($10^5$ cells/mouse).

HSPC Mobilisation

Mice bearing human CD34+ cells were surgically implanted with osmotic pumps delivering GCSF (250 μg/kg/day) for 7 days (alzet micro-osmotic pump model 1007D). At days 6 and 7, mice received intraperitoneally (IP) a single BIO5192 injection at 1 mg/kg and a single Plerixafor injection at 5 mg/kg. At the end of the mobilisation treatment, mice were engrafted with CD34+ cells stably expressing GFP and electroporated with CXCR4 and CD47 or GFP (control) mRNA to transiently overexpress the targets of interest.

Engraftment Evaluation In Vivo

Every 4 weeks after engraftment, mice were bled to evaluate human cell engraftment percentages. Blood was recovered into EDTA and stained with FACS antibodies (hCD45, CD33, CD19, CD13, CD3). Red blood cells were lysed and blood was washed with Macs buffer before FACS analysis (Canto, DIVA software).

Migration Assay

Cord Blood CD34+ cells were nucleofected with mRNA coding for CXCR4 Wild-type isoform I or CXCR4 Whim isoform I or GFP (control) allowing transient overexpression of the genes of interest. One day after culture the levels of CXCR4 expression were evaluated by FACS analysis and a migration assay was performed. Cells were seeded on the upper chamber of a transwell plate. The lower chamber contained the ligand of CXCR4 (CXCL12). 30 minutes after incubation, the number of cells in the lower chamber (migrating cells) was evaluated.

Results

Potential targets were exploited for transiently endowing edited haematopoietic stem and progenitor cells (HSPCs) with engraftment and/or growth advantage in vivo. We overexpressed genes with established functions in HSPCs, such as CD47 and CXCR4 expressed at the HSPC membrane and involved in phagocytosis protection and homing, respectively.

Figure 6:
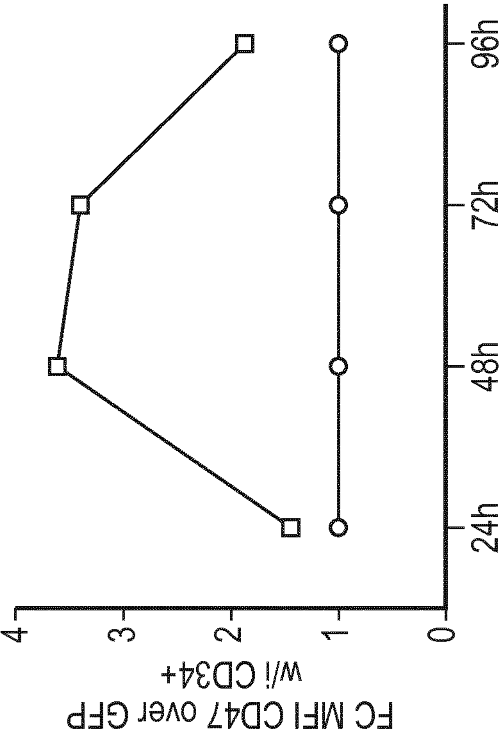
Figure 6:
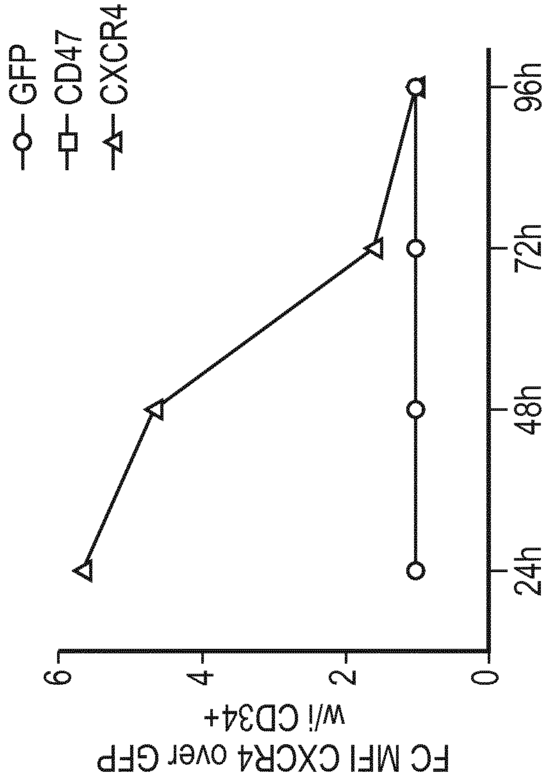

First, we measured, by FACs analysis, the expression levels of the two targets of interest after nucleofection with mRNAs. Cells were able to overexpress the two selected targets up to 6 fold increase as compared to the control (GFP) counterpart (FIG. 6).

Figure 7:
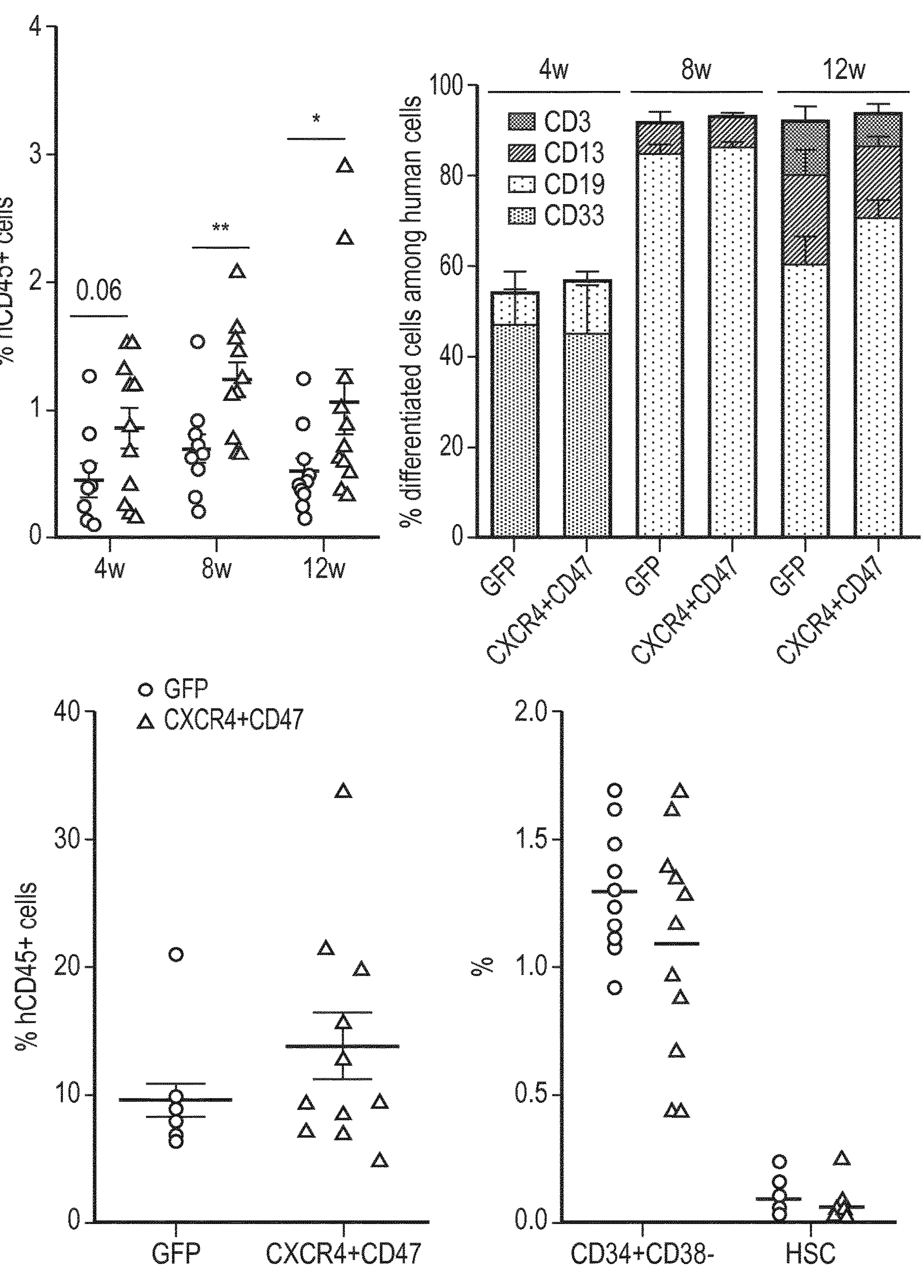

We measured biological advantages of CD47 and CXCR4 transient overexpression (OE) by scoring overall engraftment of the treated cells in NSG competitive transplantation. Results obtained with HSPCs that transiently overexpress CXCR4 and CD47 show significantly increased early engraftment without significantly affecting lineage reconstitution, and a promising increase at long term compared to control (FIG. 7).

Transient overexpression of CD47 and CXCR4 gives an engraftment advantage in vivo.

These targets were then used to favour exchange and/or selective engraftment and expansion of the advantaged HSPCs during treatment inducing mobilisation of endogenous HSPCs.

We established an experimental model to study human HSPC mobilisation from the bone marrow (BM) niche in NSGW41 mice based on drugs currently used in clinic (GCSF, Plerixafor) (Domingues et al. (2016) Int J Hematol; Welschinger, R. et al. (2013) Exp Hematol 41: 293-302.e1).

Figure 8:
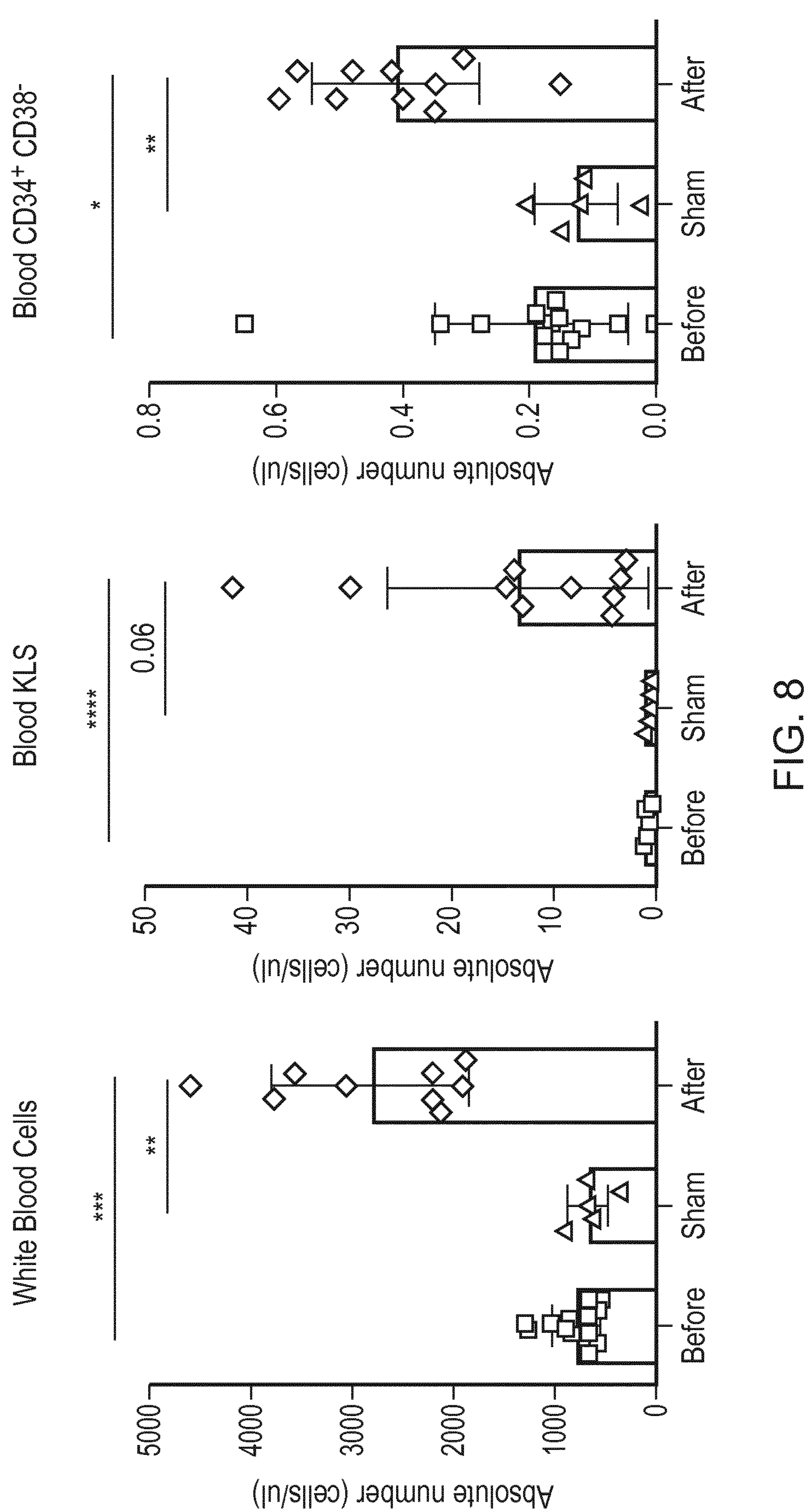

Briefly, NSGW41 mice were first engrafted with CD34+ cells in order to pre-establish a human haematochimeric graft. Mice were then treated with the conditioning agents for mobilisation (see Methods, HSPC Mobilisation). We confirmed in vivo our HSPC mobilisation protocol on mobilised Peripheral Blood CD34+ cells in NSGW41 mice, with a significant increase in number of circulating progenitor human cells (CD34+CD38−) and murine stem cells (Kit+; Lin−, Sca1+, KLS) (FIG. 8).

Figure 9:
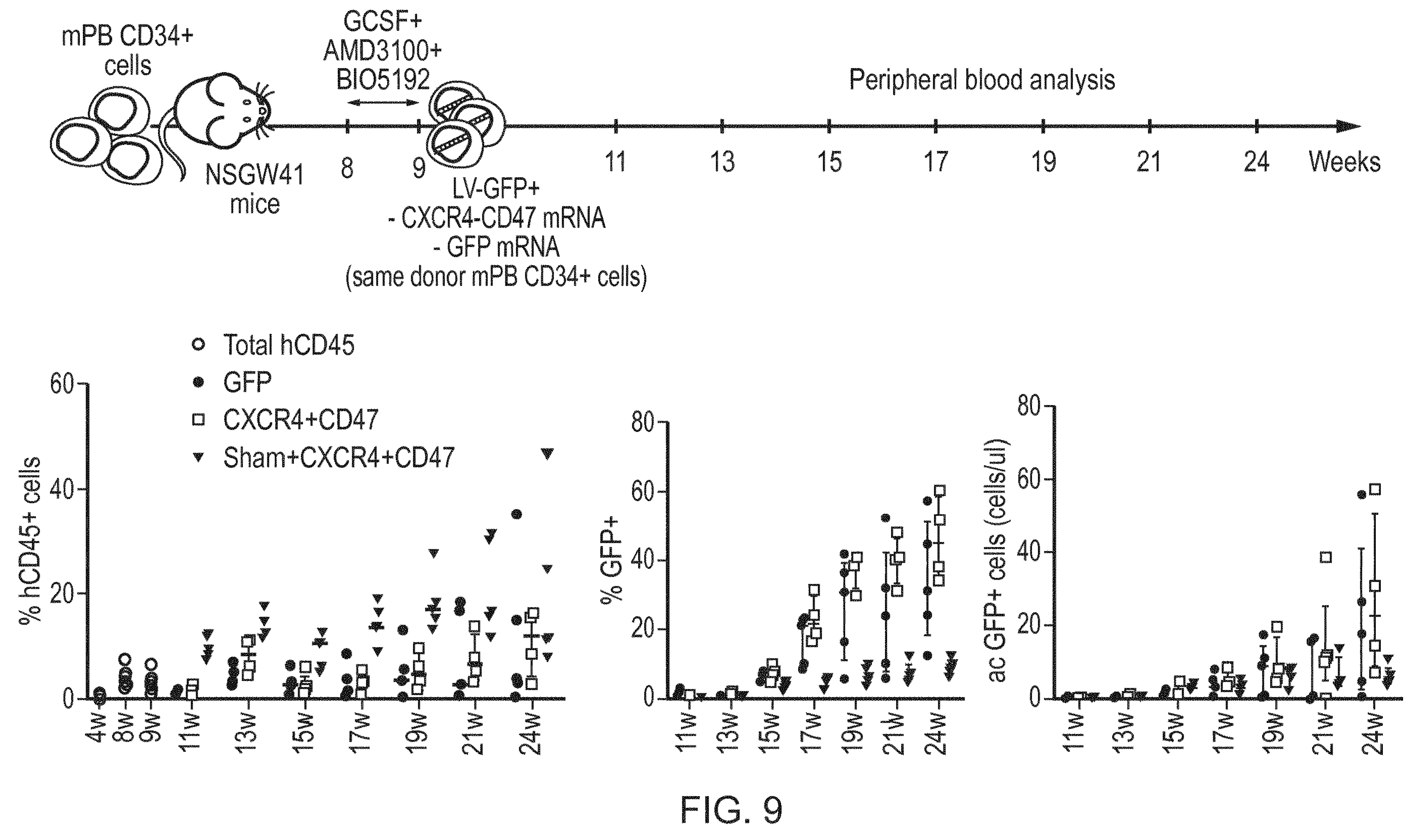

As our mobilisation protocol includes the injection of Plerixafor (also known as AMD3100), a specific antagonist of CXCR4 receptor, we decided to match CXCR4 overexpression advantage to Plerixafor mobilisation. As, after preliminary in vivo results the combination of the two targets showed an advantage in the engraftment, we evaluated human HSPC mobilisation from the bone marrow niche followed by infusion of enhanced HSPCs (CXCR4 and CD47 transient overexpression) from the same/matching donors as the original graft. NSGW41 mice stably engrafted with human HSPC were treated for mobilisation (GCSF 250 μg/kg/day for 7 days with osmotic pumps; Plerixafor 5 mg/kg/day and BIO5192 1 mg/kg/day the last two days by IP injections [BIO5192, Ramirez, et al. (2009) Blood 114: 1340-1343]) then infused with GFP marked CD34+ cells transiently overexpressing a control mRNA or CXCR4 and CD47 from the same donor as the original transplant (FIG. 9). Remarkably, CXCR4-overexpressing cells efficiently outcompeted the mobilised HSPCs and established stable chimerism at ≥40% in the human cell graft, while control cells were only detectable at 25% level (FIG. 9).

Figure 10:
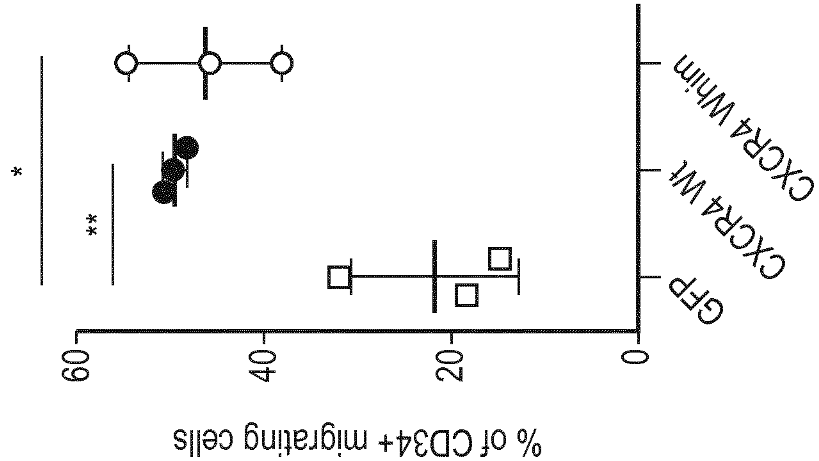
Figure 10:
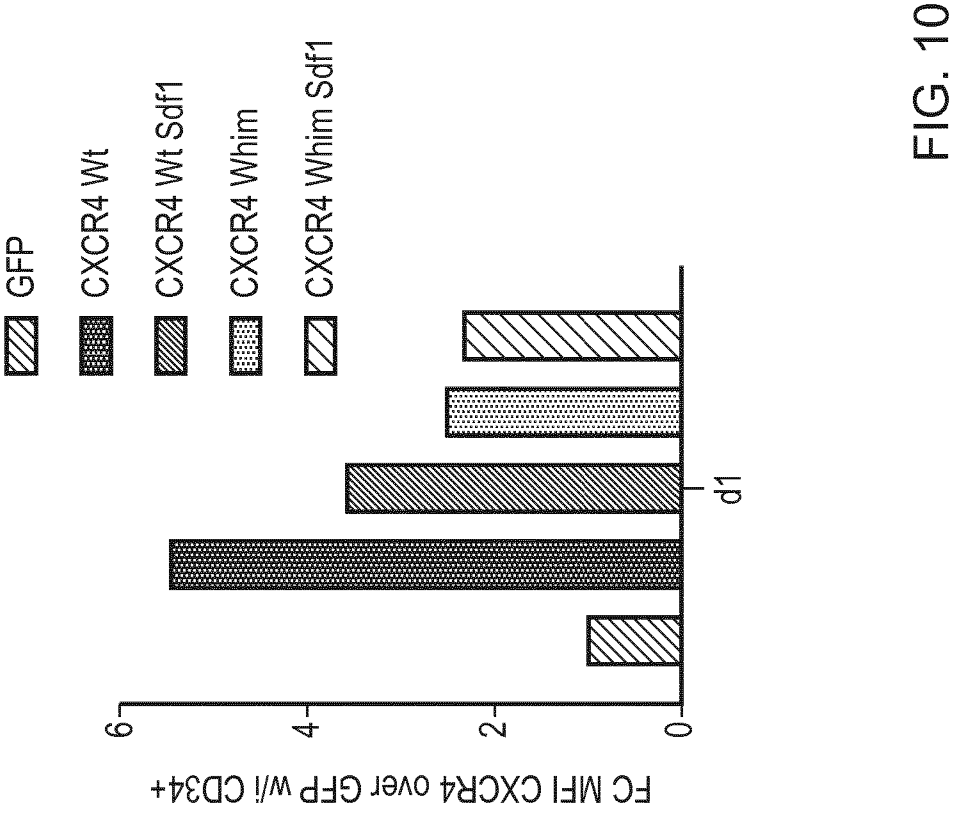

In order to increase even more the efficacy of engraftment we considered lengthening the transient window of overexpression of CXCR4. To do so, we used a truncated form of CXCR4: CXCR4 Whim isoform I that is hyperactive to its ligand (CXCL12) and which recycles less on the membrane. We performed a validation in vitro of the functionality of this modified target by a migration assay (see Methods, Migration Assay). Both CXCR4 wild type and CXCR4 Whim cells were able to migrate 2.5 fold more compared to the control group (FIG. 10).

All publications mentioned in the above specification are herein incorporated by reference. Various modifications and variations of the disclosed compositions, uses and methods of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. A population of genetically engineered haematopoietic stem and/or progenitor cells (HSPCs), wherein the HSPCs are genetically engineered to transiently express CD47 and/or C-X-C chemokine receptor type 4 (CXCR4), wherein the CXCR4 is encoded by a sequence having at least 90% sequence identity to the sequence set forth in SEQ ID NO: 11.

2. The population of genetically engineered HSPCs of claim 1, wherein the HSPCs are transduced or transfected with one or more vectors encoding the CD47 and/or CXCR4.

3. The population of genetically engineered HSPCs of claim 1, wherein the HSPCs are transduced or transfected with one or more vectors encoding the CD47 and/or CXCR4, and wherein the one or more vectors are RNA vectors, integration-defective lentiviral vectors (IDLVs), adeno-associated viral (AAV) vectors, or Sendai viral vectors.

4. The population of genetically engineered HSPCs of claim 1, wherein the HSPCs are transfected with one or more mRNAs encoding the CD47 and/or CXCR4.

5. The population of genetically engineered HSPCs of claim 1, wherein the HSPCs are genetically engineered to transiently express CD47 and CXCR4.

6. The population of genetically engineered HSPCs of claim 1, wherein the HSPCs are further genetically engineered to express a nucleotide of interest.

7. A pharmaceutical composition comprising the population of genetically engineered haematopoietic stem and/or progenitor cells (HSPCs) of claim 1 and a pharmaceutically acceptable carrier, diluent, or excipient.

8. The population of genetically engineered HSPCs of claim 5, wherein the nucleotide of interest gives rise to a therapeutic effect.

* * * * *